US011213435B2

(12) United States Patent
Fukae et al.

(10) Patent No.: US 11,213,435 B2
(45) Date of Patent: Jan. 4, 2022

(54) UNDERPANTS-TYPE DISPOSABLE DIAPER

(71) Applicant: Daio Paper Corporation, Ehime (JP)

(72) Inventors: Akinori Fukae, Ehime (JP); Yosuke Mori, Ehime (JP); Aya Ide, Ehime (JP)

(73) Assignee: Daio Paper Corporation, Ehime (JP)

( * ) Notice: Subject to any disclaimer, the term of this patent is extended or adjusted under 35 U.S.C. 154(b) by 560 days.

(21) Appl. No.: 16/303,238

(22) PCT Filed: May 11, 2017

(86) PCT No.: PCT/JP2017/017808
§ 371 (c)(1),
(2) Date: Nov. 20, 2018

(87) PCT Pub. No.: WO2017/212856
PCT Pub. Date: Dec. 14, 2017

(65) Prior Publication Data
US 2019/0201253 A1    Jul. 4, 2019

(30) Foreign Application Priority Data

Jun. 9, 2016 (JP) .............................. JP2016-115598

(51) Int. Cl.
*A61F 13/15*  (2006.01)
*A61F 13/496* (2006.01)
(Continued)

(52) U.S. Cl.
CPC .............. *A61F 13/496* (2013.01); *A61F 5/44* (2013.01); *A61F 13/49* (2013.01); *A61F 13/494* (2013.01);
(Continued)

(58) Field of Classification Search
CPC ........ A61F 13/496; A61F 13/49; A61F 13/51; A61F 13/514; A61F 13/51121; A61F 5/44; A61F 5/4401; A61F 2005/4402
See application file for complete search history.

(56) References Cited

U.S. PATENT DOCUMENTS 5,571,096 A  *  11/1996  Dobrin ................ A61F 13/5146
                                                        604/383
2011/0024940 A1    2/2011  Qureshi et al.
(Continued)

FOREIGN PATENT DOCUMENTS

CN    102470542    5/2012
CN    204951356    1/2016
(Continued)

OTHER PUBLICATIONS

International Search Report for PCT/JP2017/017808, dated Jul. 18, 2017.

*Primary Examiner* — Jacqueline F Stephens
(74) *Attorney, Agent, or Firm* — Andrus Intellectual Property Law, LLP

(57) ABSTRACT

A cover nonwoven fabric covers a back surface of an inner member from between a front side outer member and the inner member to between a back side outer member and the inner member. In this cover nonwoven fabric, a large number of holes are provided at intervals. The holes penetrate the front surface and back surface from between the front side outer member and the inner member to between the back side outer member and the inner member. The front side outer member and the back side outer member have, at least at portions overlapping with the cover nonwoven fabric and not having any elastic member, a total luminous transmittance of 50% or more.

8 Claims, 17 Drawing Sheets

(51) Int. Cl.
*A61F 13/494* (2006.01)
*A61F 13/514* (2006.01)
*A61F 5/44* (2006.01)
*A61F 13/51* (2006.01)
*A61F 13/49* (2006.01)
*A61F 13/511* (2006.01)

(52) U.S. Cl.
CPC ............ *A61F 13/51* (2013.01); *A61F 13/514* (2013.01); *A61F 5/4401* (2013.01); *A61F 13/51121* (2013.01); *A61F 2005/4402* (2013.01)

(56) References Cited

U.S. PATENT DOCUMENTS

2012/0157948 A1* 6/2012 Nhan ...................... A61F 13/42 604/361
2012/0283682 A1* 11/2012 Otsubo ............ A61F 13/49009 604/385.01
2013/0317471 A1 11/2013 Morimoto et al.
2017/0065463 A1 3/2017 Mori et al.
2017/0189244 A1 7/2017 Mueller et al.

FOREIGN PATENT DOCUMENTS

| | | |
|---|---|---|
| EP | 2526912 | 11/2012 |
| JP | 3-251245 A | 11/1991 |
| JP | 200825083 A | 2/2008 |
| JP | 2009-160129 | 7/2009 |
| JP | 2011-147516 | 8/2011 |
| JP | 2011225000 A | 11/2011 |
| JP | 2013-500175 | 1/2013 |
| JP | 2015128573 A | 7/2015 |
| JP | 2015192862 A | 11/2015 |
| KR | 2012-0118472 | 10/2012 |
| WO | 2013/167179 | 11/2013 |
| WO | 2015/137129 | 9/2015 |
| WO | 2016/048337 | 3/2016 |

* cited by examiner (a)

(b)

(c)

(a)

(b)

(c)

UNDERPANTS-TYPE DISPOSABLE DIAPER

CROSS-REFERENCE TO RELATED APPLICATIONS

This application is the U.S. national stage application of International Application PCT/JP2017/017808, filed May 11, 2017, which international application was published on Dec. 14, 2017, as International Publication WO 2017/212856 in the Japanese language. The International Application claims priority of Japanese Patent Application No. 2016-115598, filed Jun. 9, 2016. The international application and Japanese application are both incorporated herein by reference, in entirety.

TECHNICAL FIELD

The present invention relates to an underpants-type disposable diaper.

BACKGROUND ART

As for underpants-type disposable diapers, an outer member one unit-type and an outer member separated-type are known. An inner member incorporating an absorber is attached to an outer member continuously extending throughout the whole front-back direction in the outer member one unit-type. In the outer member separated-type, a front side outer member disposed in a front body and a back side outer member disposed in a back body are separately provided, and the front side outer member and the back side outer member are spaced apart in the front-back direction at the middle in the front-back direction. The inner member including the absorber extends in the front-back direction from the front side outer member to the back side outer member and is joined to the front side outer member and to the back side outer member. As an outer member, it is common to use a nonwoven fabric to ensure air permeability with an outer surface like a cloth. Particularly, in the outer member separated-type underpants-type disposable diaper, since an inner member is exposed between a front side outer member and a back side outer member, it is known to provide a cover nonwoven fabric covering a back surface of the inner member such that a liquid impervious sheet is not exposed on the back surface of the inner member.

Recently, to further improve air permeability in disposable diapers, it has been proposed to use a perforated nonwoven fabric in which a large number of holes are formed at intervals as a nonwoven fabric used for an outer member (refer to Patent Literature 1). Such a perforated nonwoven fabric has an effect of adding functional beauty in air permeability improvement, such that it is extremely important to visually recognize the presence of holes (visual effect). In this point, since Patent Literature 1 discloses an outer member one unit-type, when a perforated nonwoven fabric is used for a nonwoven fabric of an outer member, almost all holes can be visually recognized.

However, when a perforated nonwoven fabric is used for a cover nonwoven fabric to improve air permeability of a crotch portion of the outer member separated-type underpants-type disposable diaper, the front portion and the back portion of the cover nonwoven fabric are hidden by a front side outer member and a back side outer member. Therefore, even if a perforated nonwoven fabric is provided in this cover nonwoven fabric, since a user cannot visually recognize the presence of this hole, it is likely to be misunderstood that the air-permeability-improving function is provided only in the portion between the front side outer member and the back side outer member. In this case, the visual effect is not sufficiently exhibited, and there is a problem that the air-permeability-improving function which is a product feature is not correctly known to users.

CITATION LIST

Patent Literature

Patent Literature 1: JP 2015-128573 A

SUMMARY OF INVENTION

Technical Problem

In view of the above, a main object of the present invention is to improve the visual effect of holes when a perforated nonwoven fabric is used for a cover nonwoven fabric in an outer member separated-type underpants-type disposable diaper.

Solution to Problem

The representative aspects of the present invention that have solved the above problems will be described below.

First Aspect

An underpants-type disposable diaper, in which a front side outer member disposed in a front body and a back side outer member disposed in a back body are separately provided, the front side outer member and the back side outer member are spaced apart in the front-back direction at the middle in the front-back direction, an inner member having a liquid pervious top sheet, a liquid impervious sheet, and an absorber interposed therebetween extends in the front-back direction from the front side outer member to the back side outer member, the inner member is joined to each of the front side outer member and the back side outer member, a cover nonwoven fabric covering a back surface of the inner member is provided from between the front side outer member and the inner member to between the back side outer member and the inner member, both sides of the front side outer member and both sides of the back side outer member are joined to each other, a waist opening and a pair of right and left leg openings are included, and elastic members are incorporated in the front side outer member and the back side outer member, wherein the cover nonwoven fabric is provided with a plurality of holes penetrating a front surface and a back surface of the cover nonwoven fabric from between the front side outer member and the inner member to between the back side outer member and the inner member at intervals, and the front side outer member and the back side outer member have, at least at portions overlapping with the cover nonwoven fabric and not having any elastic member, a total luminous transmittance of 50% or more.

Function and Effect

As described above, the front side outer member and the back side outer member have, at least at portions overlapping with the cover nonwoven fabric and not having any elastic member, a total luminous transmittance of 50% or more. Therefore, even in portions of the cover nonwoven fabric, which are hidden by the front side outer member and the back side outer member, the holes of the perforated nonwoven fabric are transparent and can be visually recognized sufficiently, and a user can recognize that in the cover nonwoven fabric, not only a portion between the front side outer member and the back side outer member but also front and back sides of this portion have air-permeability-improving function. Therefore, the visual effect of the holes is sufficiently exhibited, and the air-permeability-improving function which is a product feature is properly known to a user.

Second Aspect

The underpants-type disposable diaper according to the first aspect, comprising inner decorative printing, which is visible on outer surfaces of the front side outer member and the back side outer member, on the liquid impervious sheet at least in a region thereof, which overlaps the front side outer member and the back side outer member, wherein the inner decorative printing overlaps with the holes at least in a part of the cover nonwoven fabric.

Function and Effect

In the underpants-type disposable diaper, decorative printing (inner decorative printing) such as characters and patterns may be provided on the liquid impervious sheet so as to be visible on a product outer surface. Through the using of such decorative printing, when the inner decorative printing and the holes at least in a part of the cover nonwoven fabric are overlapped, the holes of the perforated nonwoven fabric emerge on a background of the inner decorative printing, and it is preferable since the holes are likely to be seen through the outer surface.

Third Aspect

The underpants-type disposable diaper according to the second aspect, wherein at least either of a region where the front side outer member and the cover nonwoven fabric overlap with each other and a region where the back side outer member and the cover nonwoven fabric overlap with each other includes, on an outer side of the cover nonwoven fabric, a portion provided with an outer decorative sheet having outer decorative printing and a portion not having the outer decorative sheet.

Function and Effect

Since the inner decorative printing described before is covered with the perforated nonwoven fabric, the appearance as a decoration may be deteriorated. Therefore, for the decoration emphasizing the appearance, it is desirable to separately provide the outer decorative sheet as described above and to add the outer decorative printing there.

Fourth Aspect

The underpants-type disposable diaper according to the third aspect, wherein the inner decorative printing is a continuous decorative printing comprising a plurality of elements regularly repeating in the front-back direction and the width direction, and the outer decorative printing is an intermittent decorative printing arranged only in one or both of front and back sides of a product.

Function and Effect

Decorative printing in an underpants-type disposable diaper is not limited to a continuous decorative printing consisting of a large number of elements such as letters and pictures which are regularly repeated in the front-back direction and the width direction and may be an intermittent decorative printing arranged only in one or both of the front and back sides of the product such as product logos, pictures of characters, and the like. The continuous decorative printing is a repetition of a large number of elements, and there is almost no influence on appearance even as a background of the perforated nonwoven fabric. However, when the intermittent decorative printing is covered with the perforated nonwoven fabric, there is a difference in appearance between portions having the holes and the other portions, and the intermittent decorative printing is partly hidden due to high concealing property of edge portions of the holes. Consequently, the deterioration of appearance becomes remarkable. Therefore, it is desirable to distinguish a member having the inner decorative printing and a member having the outer decorative printing, and, as described above, to apply the continuous decorative printing to the inner decorative printing and apply the intermittent decorative printing to the outer decorative printing.

Fifth Aspect

The underpants-type disposable diaper according to any one of the first to fourth aspects, wherein at least either of the front side outer member and the back side outer member is joined to the inner member, at regions overlapping with both end portions in the width direction of the inner member, and is not joined or is intermittently and peelably joined to the inner member, at a part on a crotch side or a whole part in the front-back direction of a region between the regions overlapping with the both end portions in the width direction of the inner member.

Function and Effect

In this manner, since the portion joining the inner member and at least one of the front side outer member and the back side outer member is not joined or is intermittently and peelably joined, at the part on the crotch side or at the whole part throughout in the front-back direction, gaps formed between the inner member and at least one of the front side outer member and the back side outer member communicate with the crotch side and improve air permeability. In addition, since the cover nonwoven fabric (perforated nonwoven fabric) hidden by at least one of the front side outer member and the back side outer member can be directly seen by pulling up this part, the higher visual effect of the holes can be obtained.

Sixth Aspect

The underpants-type disposable diaper according to any one of the first to fifth aspects, comprising side gathers extending from both sides of the inner member so as to be in contact with the legs of a wearer and each of the side gathers having a base end on a side portion on a back surface side of the liquid impervious sheet in the inner member, and a gather nonwoven fabric forming an outer surface at least from the base end to a tip end, wherein the cover nonwoven fabric extends at least from between a base portion of one of the side gathers and the liquid impervious sheet to between a base portion of the other side gather and the liquid imperious sheet, and the gather nonwoven fabric has a total luminous transmittance of 60 to 90%.

Function and Effect

When the side edges of the cover nonwoven fabric are covered with the gather nonwoven fabrics of the side gathers as described before, the side edges of the cover nonwoven fabric are unlikely to contact the legs of the wearer, and the side edges of the gather nonwoven fabric also face toward the center in the width direction and are unlikely to contact the legs of the wearer. As a result, it is obvious that the texture improves, and there is little risk that the side portions of the cover nonwoven fabric are peeled off by movement of the legs. In this case, the liquid impervious sheet is concealed by the cover nonwoven fabrics and the gather nonwoven fabric, and the side portions of the cover nonwoven fabric are covered with the gather nonwoven fabrics. However, when the total luminous transmittance of the gather nonwoven fabric is 60 to 90%, even in the portions where the gather nonwoven fabrics hide the cover nonwoven fabric, since the holes of the perforated nonwoven fabric are transparent and can be visually recognized sufficiently, it can be recognized that a portion having the air-permeability-improving function extends to the side gathers, and the visual effect of the holes can be sufficiently exhibited.

Advantageous Effects of Invention

As described above, the present invention provides advantages such as improving the visual effect of holes when a perforated nonwoven fabric is used for a cover nonwoven fabric in an outer member separated-type underpants-type disposable diaper.

DESCRIPTION OF EMBODIMENTS

Figure 1:
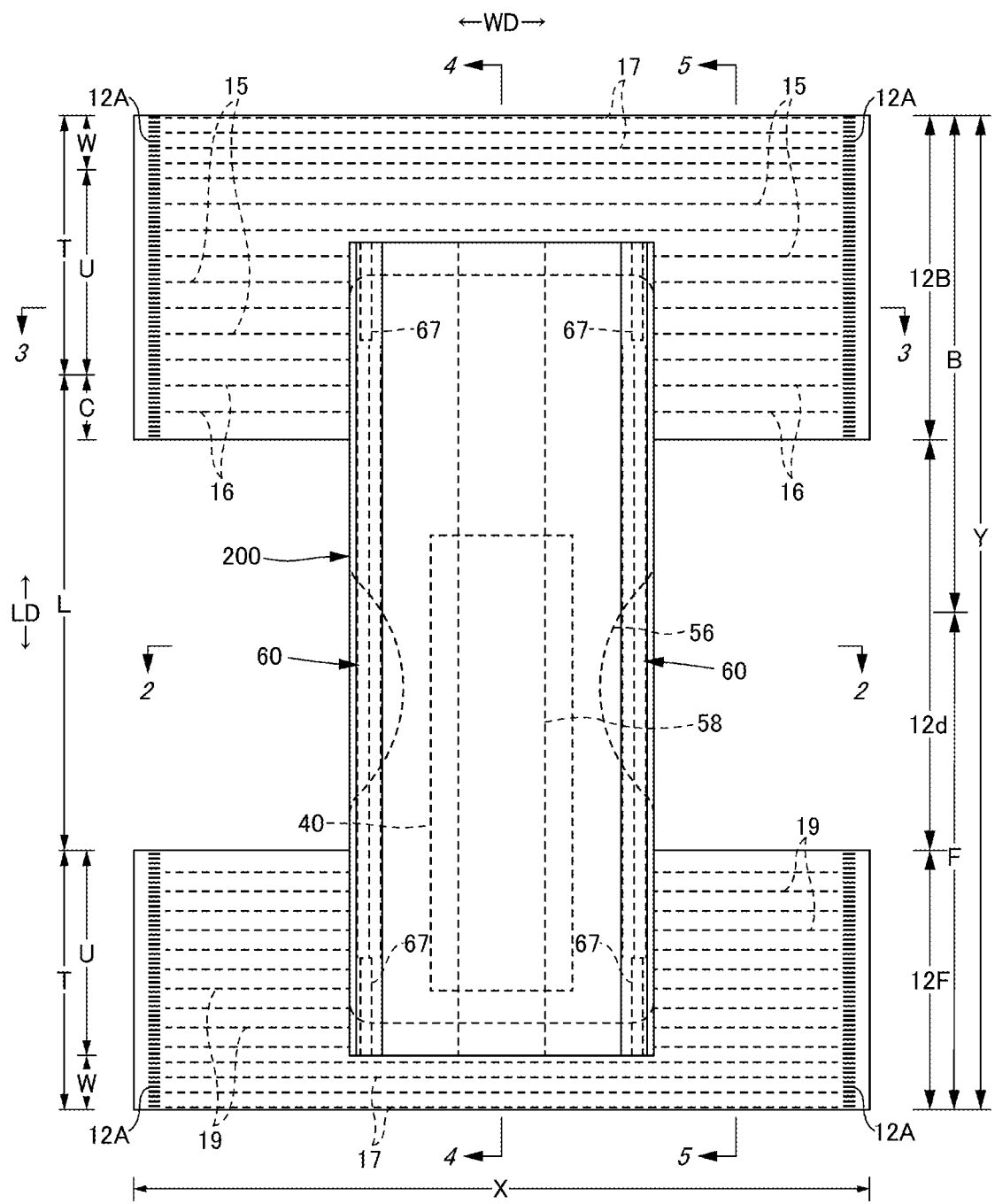
FIG. 1 is a plan view of an inner surface of an underpants-type disposable diaper in a spread state.

Hereinafter, embodiments of the present invention will be described in detail with reference to the accompanying drawings. A dotted pattern portion in the cross-sectional view indicates an adhesive as joining means for joining constituent members positioned on a front surface side and a back surface side thereof. The dotted pattern portion is formed by solid, bead, curtain, summit, or spiral application of a hot melt adhesive, pattern coating (transfer of a hot melt adhesive in a letterpress method), or the like. Alternatively, in a fixed portion of each elastic member, instead of or together with the above, the dotted pattern is formed by application with a comb gun or a SureWrap nozzle on an outer peripheral surface of the elastic member. Examples of the hot melt adhesive include, but are not limited to, adhesives of the EVA type, adhesive rubber type (elastomer), olefin, and polyester/polyamide. As a joining means for joining each constituent member, a means by material welding such as heat sealing or ultrasonic sealing can also be used.

FIGS. 1 to 6 illustrate an underpants-type disposable diaper. This underpants-type disposable diaper includes a front side outer member 12F disposed in a front body F, a back side outer member 12B disposed in a back body B, and an inner member 200 provided inside of the outer members 12F and 12B so as to extend from the front side outer member 12F to the back side outer member 12B through a crotch portion. Side seal portions 12A are formed by joining both sides of the front side outer member 12F and both side of the back side outer member 12B. Therefore, an opening formed by front and back end portions of the outer members 12F and 12B becomes a waist opening WO through which the lower torso of a wearer passes and portions surrounded by lower edges of the outer members 12F and 12B and side edges of the inner member 200 on both sides of the inner member 200 in the width direction become leg openings LO through which the legs pass. The inner member 200 is a portion that absorbs and holds excrement such as urine, and the outer members 12F and 12B are portions for supporting the inner member 200 with respect to the body of a wearer. The reference sign Y denotes the maximum length of a diaper in a spread state (the length in the front-back direction from an edge of the waist opening WO of the front body F to an edge of the waist opening WO of the back body B), and the reference sign X denotes the maximum width of a diaper in a spread state.

In addition, the underpants-type disposable diaper of this embodiment includes a lower torso region T and an intermediate region L. The lower torso region T is defined as a range in the front-back direction having side seal portions 12A (a region in the front-back direction from the waist opening WO to upper ends of the leg openings LO). The intermediate region L is defined as a range in the front-back direction of a portion forming the leg openings LO (between the region in the front-back direction having the side seal portions 12A of the front body F and the region in the front-back direction having the side seal portions 12A of the back body B). The lower torso region T can be divided into a "waist portion" W which conceptually forms an edge portion of a waist opening and an "under-waist portion" U which is a portion lower than the waist portion W. Normally, in the case of having a boundary where stretching stress in the width direction WD changes in the lower torso region T (for example, in the case where the fineness and stretch rate of each elastic members change), a portion nearer to the waist opening WO than a boundary closest to the waist opening WO is the waist portion W. When there is no such boundary, the waist opening WO side of an absorber 56 or the inner member 200 is the waist portion W. A length in the front-back direction varies depending on the size of a product and can be appropriately determined. For example, the waist portion W can be set to 15 to 40 mm, and the under-waist portion U can be set to 65 to 120 mm. On the other hand, both side edges of the intermediate region L are narrowed along the periphery of the legs of a wearer in a channel shape or a curved shape to form portions through which the wearer's legs pass. As a result, the underpants-type disposable diaper in a spread state has a substantially hourglass shape as a whole.

(Inner Member)

Figure 3:
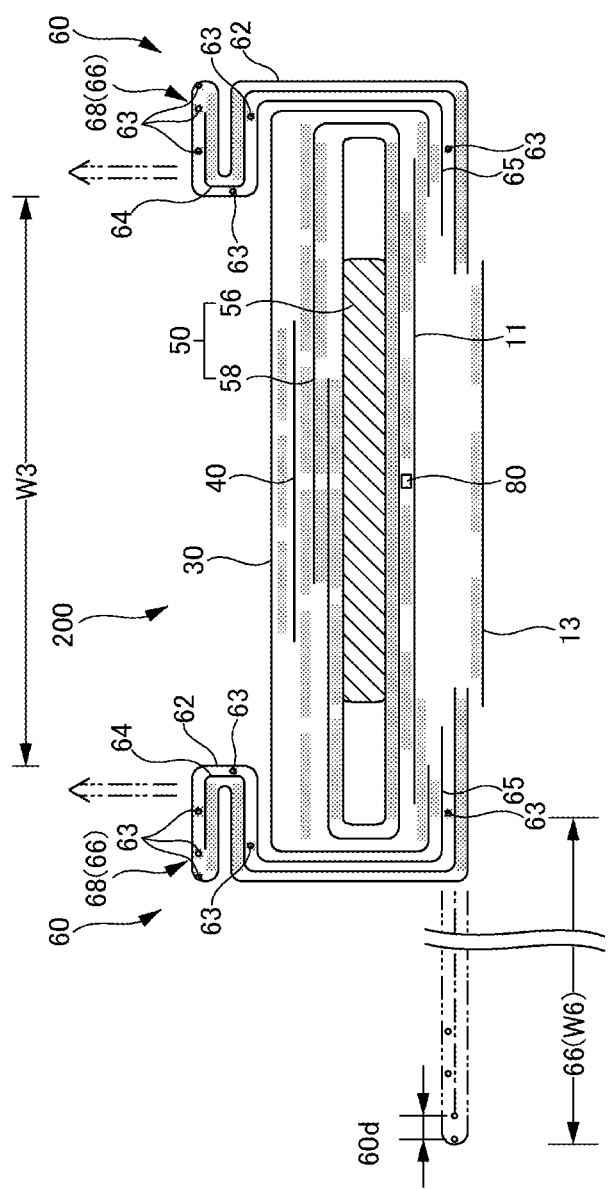
FIG. 3 is a cross-sectional view taken along line 2-2 in FIG. 1.
Figure 4:
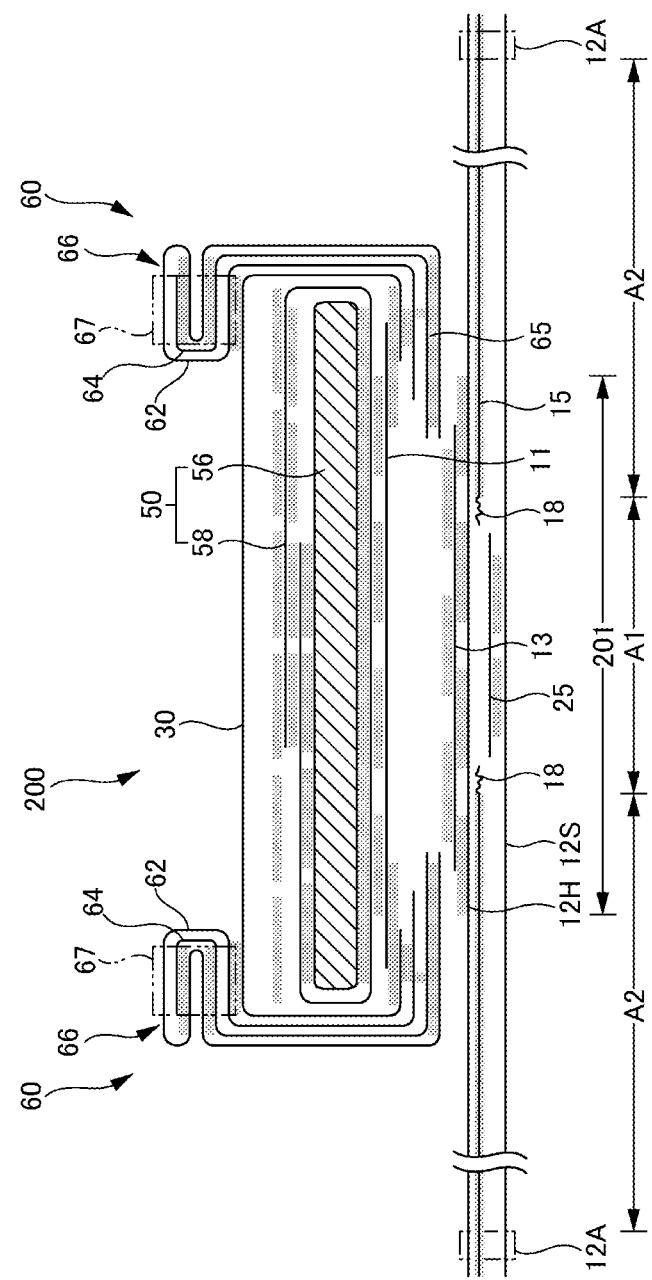
FIG. 4 is a cross-sectional view taken along line 3-3 in FIG. 1.
Figure 5:
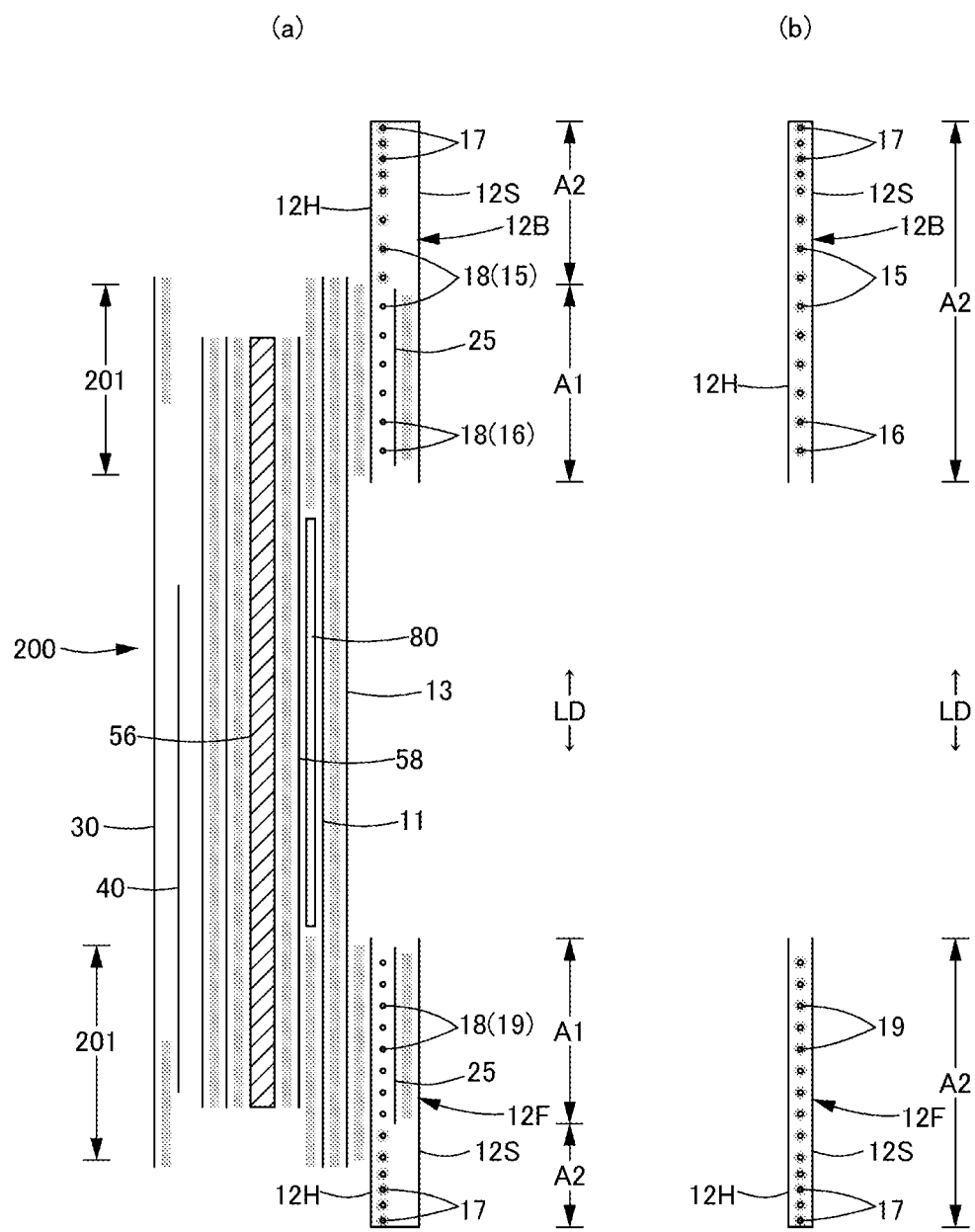
FIG. 5(a) is a cross-sectional view taken along line 4-4 in FIG. 1.
FIG. 5(b) is a cross-sectional view taken along line 5-5 in FIG. 1.
Figure 6:
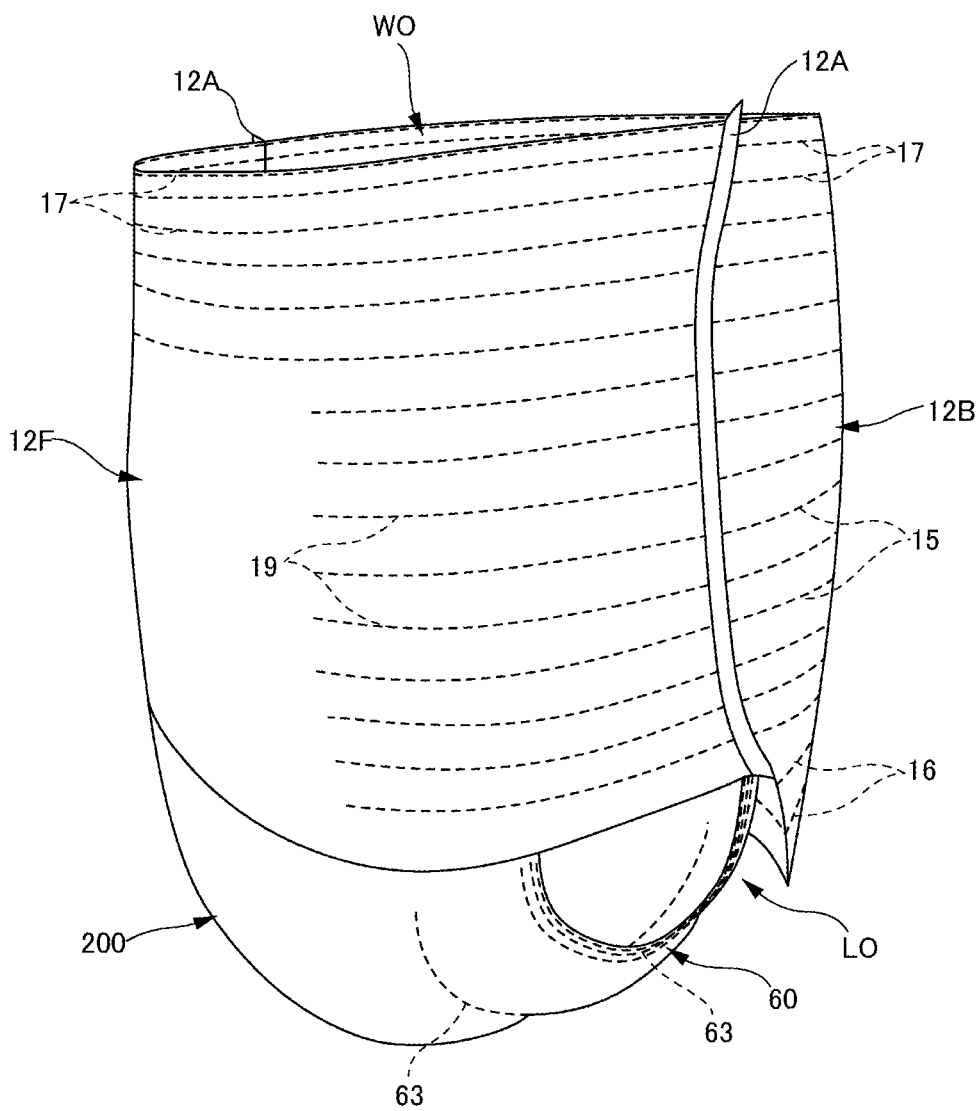
FIG. 6 is a perspective view (holes are omitted) of an underpants-type disposable diaper.

The inner member 200 can have an arbitrary shape, but in the illustrated embodiment, it is rectangular. As illustrated in FIGS. 3 to 5, the inner member 200 is provided with a top sheet 30 on the body side, a liquid impervious sheet 11, and an absorbent element 50 interposed therebetween, and is a main unit section that plays a role of an absorbent function. The reference sign 40 denotes an intermediate sheet (second sheet) provided between the top sheet 30 and the absorbent element 50 in order to promptly transfer liquid having permeated through the top sheet 30 to the absorbent element 50. The reference sign 60 denotes side gathers 60 extending from both sides of the inner member 200 so as to be in contact with the legs of a wearer in order to prevent excrement from leaking to the both sides of the inner member 200.

(Top Sheet)

The top sheet 30 has a property of permeating liquid, and examples of the top sheet 30 include a perforated or non-perforated nonwoven fabric and a porous plastic sheet. Among them, a raw fiber of the nonwoven fabric is not particularly limited. Examples of the raw fiber include synthetic fibers such as olefin such as polyethylene and polypropylene, polyester, and polyamide, regenerated fibers such as rayon and cupra, natural fibers such as cotton, and mixed fibers and composite fibers in which two or more of these are used. Further, the nonwoven fabric may be manufactured by any processing. Examples of the processing method include known methods such as a spun lace method, a spunbond method, a thermal bond method, a melt blown method, a needle punch method, an air-through method, and a point bond method. For example, if flexibility and drapeability are required, the spunbond method and the spun lace method are preferable processing methods, and if bulkiness and softness are required, the air-through method, the point bond method, and the thermal bond method are preferable processing methods.

Further, the top sheet 30 may be made of one sheet or a laminated sheet obtained by bonding two or more sheets. Similarly, the top sheet 30 may be composed of one sheet or two or more sheets with respect to the plane direction.

Both sides of the top sheet 30 may be folded back to the back surface side at side edges of the absorbent element 50 or protruded laterally beyond the side edges of the absorbent element 50 without folding back.

For the purpose of preventing positional deviation of the top sheet with respect to a member on the back surface side thereof, it is desirable that the top sheet 30 be fixed to a member adjacent to the back surface side by joining means such as heat sealing or ultrasonic sealing material welding or by a hot melt adhesive. In the illustrated embodiments, the top sheet 30 is fixed to the surface of the intermediate sheet 40 and an area on the surface of the wrapping sheet 58, which is located on a front surface side of the absorber 56, by a hot melt adhesive applied on a back surface of the top sheet 30.

(Intermediate Sheet)

In order to quickly transfer the liquid having permeated through the top sheet 30 to the absorber, it is possible to provide the intermediate sheet (also referred to as "second sheet") 40 having a higher liquid permeation rate than the top sheet 30. This intermediate sheet 40 not only improves the absorption performance by an absorber by immediately moving liquid to the absorber, but also prevents "returning" phenomenon of the absorbed liquid from the absorber to make a surface of the top sheet 30 dry constantly. The intermediate sheet 40 can also be omitted.

Examples of the intermediate sheet 40 include the same material as the top sheet 30, a spun lace, a spunbond, SMS, a pulp nonwoven fabric, a mixed sheet of pulp and rayon, a point bond, or crepe paper. In particular, an air-through nonwoven fabric is preferable because it is bulky. It is preferable to use a composite fiber having a core-sheath structure for the air-through nonwoven fabric. In this case, resin used for the core may be polypropylene (PP), but polyester (PET) having high rigidity is preferable. The basis weight is preferably 20 to 80 g/m$^2$, more preferably 25 to 60 g/m$^2$. The fineness of the raw fiber of the nonwoven fabric is preferably 2.0 to 10 dtex. To increase the bulkiness of the nonwoven fabric, it is also preferable to use eccentric fibers, hollow fibers, eccentric and hollow fibers, whose core is not in the center, as mixed fibers of all or a part of the raw material fibers.

The intermediate sheet 40 in the illustrated embodiment is disposed at the center having the width shorter than the width of the absorber 56, but may be provided throughout the maximum width of the absorber 56. The length of the intermediate sheet 40 in the longitudinal direction may be the same as the length of the absorber 56 or may be within a short length range centering on a region receiving a liquid.

For the purpose of preventing positional deviation of the intermediate sheet with respect to a member on the back surface side thereof, it is desirable that the intermediate sheet 40 be fixed to a member adjacent to the back surface side by joining means such as heat sealing or ultrasonic sealing material welding or by a hot melt adhesive. In the illustrated embodiments, the intermediate sheet 40 is fixed to the surface of an area of the wrapping sheet 58, which is positioned on a front surface side of the absorber 56, by a hot melt adhesive applied on the back surface of the intermediate sheet 40.

(Liquid Impervious Sheet)

The material of the liquid impervious sheet 11 is not particularly limited, but examples of the material include a plastic film made of an olefin resin such as polyethylene and polypropylene, a laminated nonwoven fabric having a plastic film on the surface of a nonwoven fabric, and a laminated sheet obtained by joining nonwoven fabrics or the like on a plastic film. In the liquid impervious sheet 11, it is preferable to use a material having liquid impermeability and moisture permeability that has been favorably used from the viewpoint of prevention of stuffiness. As the moisture-permeable plastic film, a microporous plastic film is widely used. The microporous plastic film is obtained by stretching a sheet in a monoaxial or biaxial direction after forming the sheet by kneading an inorganic filler in an olefin-based resin such as polyethylene or polypropylene. In addition to this, a nonwoven fabric of a micro-denier fiber and a liquid impervious sheet without a plastic film having reinforced leakage-resistance achieved by applying heat and pressure to reduce the gaps between the fibers or by application with super absorbent resin, a hydrophobic resin, or a water repellent agent can also be used as the liquid impervious sheet 11.

The liquid impervious sheet 11 may have a width that fits on the back surface side of the absorbent element 50 as illustrated in the drawing. Alternatively, to enhance leakage resistance, the liquid impervious sheet 11 may be disposed around both sides of the absorbent element 50 to extend to both sides of the surface of the top sheet 30 side of the absorbent element 50. It is appropriate that the width of this extending portion is about 5 to 20 mm for the right side and the left side.

Further, on the inside of the liquid impervious sheet 11, in particular, on the surface of the absorber 56 side, an excretion indicator that changes its color due to absorption of a liquid component can be provided.

(Side Gather)

The side gathers 60 extend throughout the whole front-back direction LD along both sides of the inner member 200 and are provided to contact the legs of a wearer and prevent side leakage. In general, the side gather 60 is a gather called a three-dimensional gather or a flat gather.

The side gathers 60 of the first embodiment illustrated in FIGS. 3 and 4 are so-called three-dimensional gathers and standing from side portions to a front surface side of the inner member 200. In each of the side gathers 60, a root-side portion stands diagonally toward the center in the width direction, and a portion closer to a tip than to the intermediate portion stands diagonally outward in the width direction, but the configuration is not limited to this and can be appropriately changed to a structure of standing toward the center in the width direction as a whole or the like.

To be more specific, the side gather 60 according to the first embodiment is formed by folding back and being folded in two, in the width direction WD at a tip portion, a belt shaped gather nonwoven fabric 62 having a length equal to the length in the front-back direction of the inner member 200, and a plurality of elongated gather elastic members 63 are fixed with intervals in the width direction WD in a stretched state along the longitudinal direction between the folded back portion and an adjacent sheet. A base portion located on the opposite side to a tip portion of the side gather 60 (the end portion on the side opposite to a sheet folded back portion in the width direction WD) is a root portion 65 fixed to a side portion on the back surface side of the liquid impervious sheet 11 in the inner member 200, and a portion other than the root portion 65 is a main unit section 66 (a portion on the folded back portion side) extending from the root portion 65. The main unit section 66 includes a base side portion directed toward the center in the width direction and a tip side portion folded back outward in the width direction from a tip of the base side portion. Although this embodiment is a surface contact-type side gather 60, a line contact-type side gather 60 which is not folded back outward in the width direction can also be used. Both end portions of the main unit section 66 in the front-back direction are set to be fallen parts 67 fixed to a surface of a side portion of the top sheet 30 in a fallen state, while an intermediate portion in the front-back direction positioned therebetween is a non-fixed free portion 68, and gather elastic members 63 along the front-back direction LD are fixed to the free portion 68 in a stretched state.

As the gather nonwoven fabric 62, a nonwoven fabric which is flexible and excellent in uniformity and concealing property such as a spunbonded nonwoven fabric (SS, SSS, etc.), SMS nonwoven fabric (SMS, SSMMS, etc.), melt-blown nonwoven fabric, and on which a water repellent process is performed by silicone as necessary, can be suitably used, and the fiber basis weight is preferably set to about 10 to 30 g/m$^2$. As the gather elastic member 63, a rubber thread or the like can be used. When a spandex rubber thread is used, the fineness is preferably 470 to 1240 dtex, more preferably 620 to 940 dtex. The stretch rate at the time of fixing is preferably 150 to 350%, more preferably 200 to 300%. The term "stretch rate" means a value when the natural length is taken as 100%. As illustrated in the drawing, a waterproof film 64 may be interposed between the gather nonwoven fabrics 62 folded in two. In this case, the gather nonwoven fabric 62 may be partially omitted in the portion where the waterproof film 64 is present. However, in order to make the appearance and feel of a product like a cloth, it is necessary that at least an outer surface from a base end to a tip of the side gather 60 is formed of the gather nonwoven fabric 62 as the illustrated embodiment.

The number of the gather elastic members 63 provided in the free portion of the side gather 60 is preferably two to six, more preferably three to five. An appropriate arrangement interval 60d is 3 to 10 mm With such a configuration, a range in which the gather elastic members 63 are disposed easily comes into surface contact with the skin. The gather elastic member 63 may be disposed not only on the tip side but also on the root side.

In the free portion 68 of the side gather 60, at least one of a hot melt adhesive by various application methods and a fixing means by material welding such as heat seal or ultrasonic seal can be used for bonding an inner layer and an outer layer of the gather nonwoven fabric 62 and for fixing the gather elastic members 63 sandwiched therebetween. Since the flexibility is impaired when the whole surface of the inner layer and whole surface of the outer layer of the gather nonwoven fabric 62 are fixed each other, it is preferable that an area other than the bonded portions of the gather elastic members 63 be not bonded or be weakly bonded. In the illustrated embodiment, by applying a hot melt adhesive only to outer peripheral surfaces of the gather elastic members 63 by an application means such as a comb gun or a SureWrap nozzle and sandwiching the gather elastic members between the inner layer and the outer layer of the gather nonwoven fabric 62, fixation of the gather elastic members 63 to the inner layer and the outer layer of the gather nonwoven fabric 62 and fixation between the inner layer and the outer layer of the gather nonwoven fabric 62 are performed by using only the hot melt adhesive applied to the outer peripheral surfaces of the gather elastic members 63.

Further, for fixation of the waterproof film 64, which has been incorporated in the side gather 60, and the gather nonwoven fabric 62 and fixation of the fallen parts 67 to the surface of the side portion of the inner member 200, at least one of a hot melt adhesive by various application methods and material welding such as heat sealing and ultrasonic sealing can be used. In the illustrated embodiment, slot application of a hot melt adhesive is used for fixing the waterproof film 64. In addition, to fix the fallen parts 67 in the illustrated embodiment, the means of a hot melt adhesive and the means of material welding are combined, but these fixation can be carried out by either one of these means.

The fixing target of the root portion 65 of the side gather 60 can be an appropriate member such as the top sheet 30, the liquid impervious sheet 11, and the absorbent element 50 in the inner member 200.

In the side gather 60 according to the first embodiment formed as described above, a contraction force of the gather elastic members 63 acts so as to bring both end portions of the side gather in the front-back direction close to each other, but both end portions in the front-back direction of the main unit section 66 are fixed not to erect, and a space between the both ends is a non-fixed free portion. Therefore, only the free portion stands so as to come into contact with the body side as illustrated in FIG. 3 by two-dot chain line arrows. Particularly, when the root portion 65 is positioned on the back surface side of the inner member 200, the side gathers 60 stand so as to open outward in the width direction at and around a crotch portion, such that the side gathers 60 come into surface contact with a leg portion, and therefore, the fitting is improved.

Figure 12:
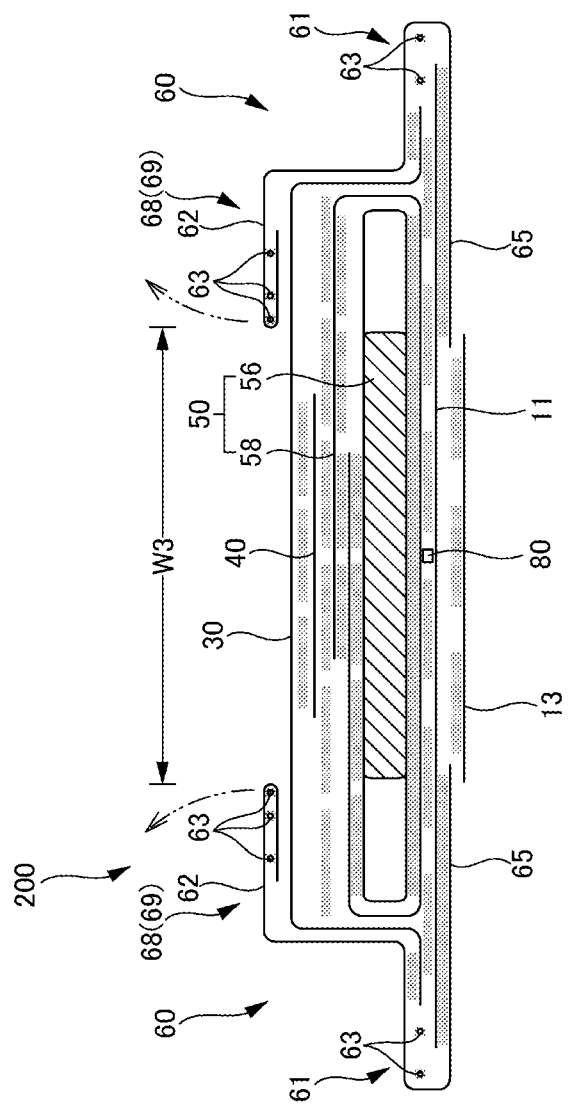
FIG. 12 is a cross-sectional view taken along line 2-2 in FIG. 1 according to another embodiment.
Figure 13:
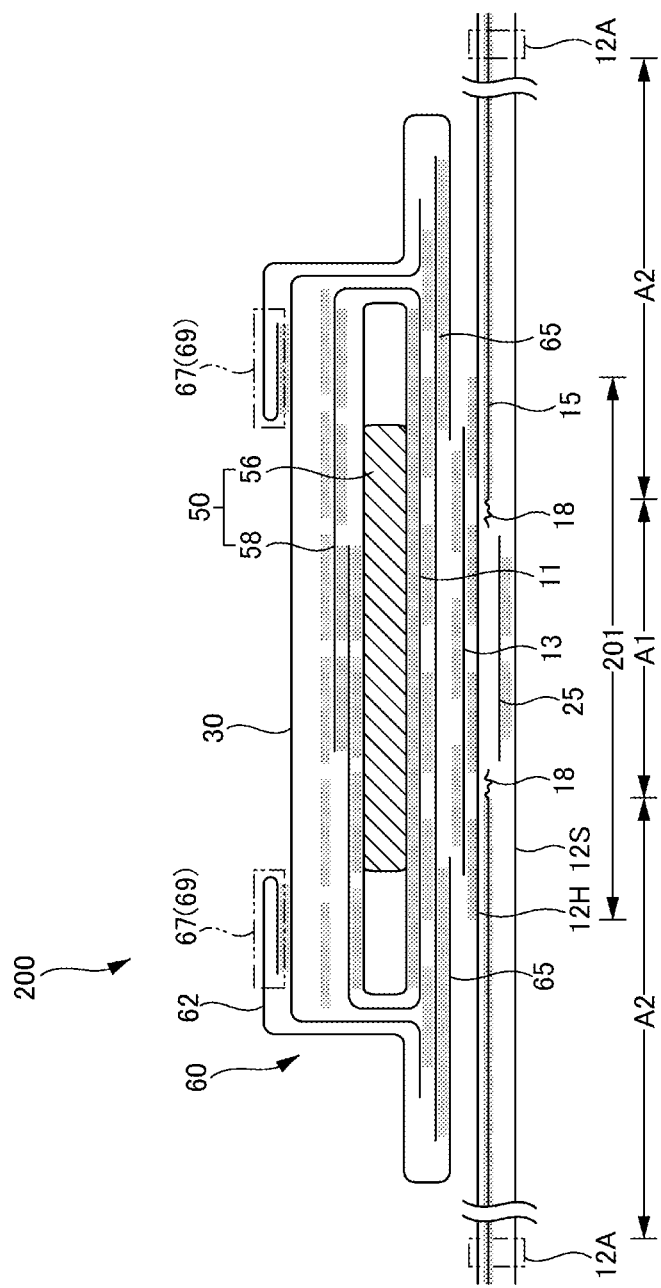
FIG. 13 is a cross-sectional view taken along line 3-3 in FIG. 1 according to another embodiment.

Although the dimension of the side gather 60 according to the first embodiment can be appropriately determined, in the case of an infant disposable diaper, as illustrated in FIG. 3, for example, the erection height of the side gather 60 (the width direction length of the main unit section 66 in a spread state) W6 is preferably 15 to 60 mm, particularly 20 to 40 mm. Further, in a state where the side gathers 60 are folded flat so as to be parallel to a surface of the top sheet 30, it is preferable that the distance W3 between the innermost folds be 60 to 190 mm, particularly 70 to 140 mm Although the side gathers 60 of the first embodiment include only three-dimensional gathers, they may include both three-dimensional gathers and flat gathers or may include only flat gathers. FIGS. 12 and 13 illustrate the side gathers 60 according to the second embodiment, including both three-dimensional gathers and flat gathers. Each of the side gathers 60 has a first portion 61 (flat gather portion) and a second portion 69 (three-dimensional gather portion). The first portion 61 protrudes to the side of the inner member 200 from the root portion 65 fixed to a side portion of the inner member 200 on the back surface side of the liquid impervious sheet 11. The second portion 69 protrudes to the front surface side of the inner member 200 from a portion of the root portion 65 fixed to each of both sides of the top sheet 30 in the inner member 200. More specifically, a belt shaped gather nonwoven fabric 62 having a length equal to the length in the front-back direction of the inner member 200 extends laterally from the root portion 65 and is folded back to the front surface side at a tip of the first portion 61, and the portion folded back to the front surface side reaches the second portion 69 via the first portion 61 and is folded back at a tip of the second portion 69. In the folded portion of the gather nonwoven fabric 62, opposing portions are joined by a hot melt adhesive or the like. Further, both end portions in the front-back direction of the second portion 69 are the fallen parts 67 fixed to a side surface of the top sheet 30 in a fallen state. On the other hand, the intermediate portion in the front-back direction positioned between the both ends is a non-fixed free portion 68. At least in the intermediate portion in the front-back direction of the first portion 61 and in the free portion 68 of the second portion 69, one gather elastic member 63 or a plurality of the gather elastic members 63 with intervals in the width direction WD are fixed in a stretched state along the front-back direction LD. Due to a contraction force thereof, the free portion 68 of the second portion 69 contracts in the front-back direction LD and becomes a three-dimensional gather in contact with the leg, and also the first portion 61 contracts in the front-back direction LD and becomes a flat gather in contact with the leg.

Other points relating to the second embodiment, for example, a material of the gather nonwoven fabric 62, a material of the gather elastic member 63, and the like are the same as those in the first embodiment, and therefore, the description will be omitted.

(Absorbent Element)

The absorbent element 50 has the absorber 56 and a wrapping sheet 58 wrapping the entire absorber 56. The wrapping sheet 58 can also be omitted.

(Absorber)

The absorber 56 can be formed of an assembly of fibers. As this fiber assembly, besides those obtained by accumulating short fibers such as fluff pulp and synthetic fibers, a filament assembly obtained by opening tows (fiber bundles) of synthetic fibers such as cellulose acetate as required can also be used. When fluff pulp or short fibers are accumulated, fiber basis weight can be set to, for example, about 100 to 300 g/m², and in the case of a filament assembly, fiber basis weight can be set to about 30 to 120 g/m². In the case of a synthetic fiber, the fineness is, for example, 1 to 16 dtex, preferably 1 to 10 dtex, more preferably 1 to 5 dtex. In the case of filament assembly, the filaments may be non-crimped fibers, but are preferably crimped fibers. The degree of crimp of the crimped fiber can be, for example, about 5 to 75 crimps, preferably about 10 to 50 crimps, and more preferably about 15 to 50 crimps per inch. In addition, crimped fibers which are uniformly crimped are often used. It is preferable to disperse and hold the super absorbent polymer particles in the absorber 56.

Figure 7:
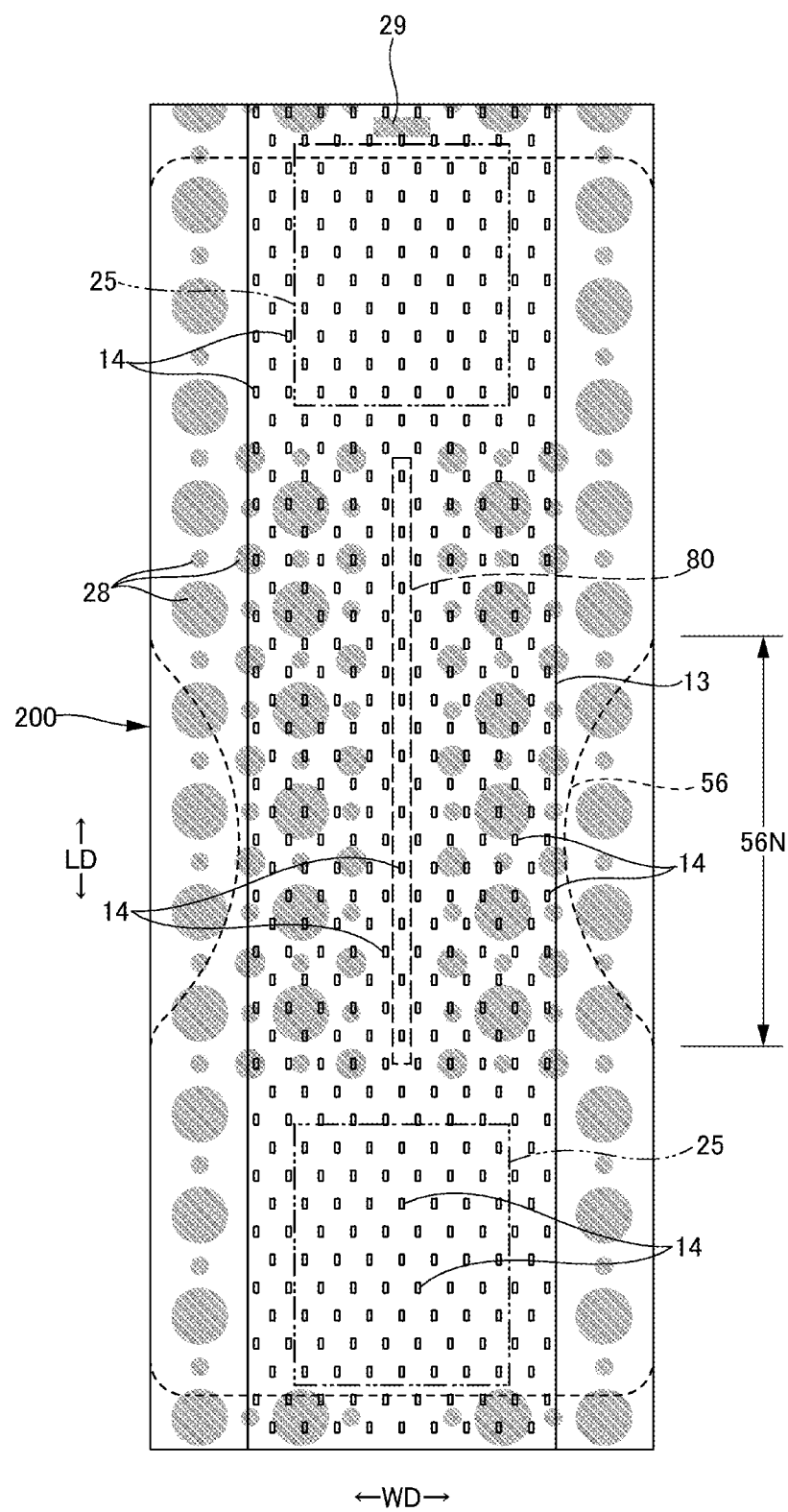
FIG. 7 is a plan view of an outer surface of an inner member in a spread state.

The absorber 56 may have a rectangular shape, and, as illustrated in FIG. 7, preferably has a shape similar to the outline of an hourglass which has a front end portion, a back end portion and a narrowing portion 56N positioned between the front end portion and the back end portion and having narrower width than that of the front end portion and that of the back end portion, since the fitting of the absorber 56 itself and the side gathers 60 around the legs is improved.

Further, although the size of the absorber 56 can be appropriately determined as long as the absorber 56 extends throughout the front, back, right and left sides with respect to an excreted position of urine, it is preferable that the absorber 56 extend to or near peripheral edge portion of the inner member 200 in the front-back direction LD and the width direction WD. The reference sign 56X denotes the width of the absorber 56.

(Super Absorbent Polymer Particle)

The absorber 56 can contain super absorbent polymer particles partially or entirely. The super absorbent polymer particle includes "powder" in addition to "particle". The super absorbent polymer particles 54 used for this kind of disposable diapers can be used as they are, and for example, screened with a sieve (shaking for 5 minutes) using a standard sieve of 500 μm (JIS Z 8801-1: 2006), and the proportion of particles remaining on the sieve is desirably 30% by weight or less. Further, the proportion of particles remaining on the sieve by screening (shaking for 5 minutes) using a standard sieve of 180 μm (JIS Z 8801-1: 2006) is desirably 60% by weight or more.

The material of the super absorbent polymer particles is not particularly limited, but materials having a water absorption capacity of 40 g/g or more are suitable. Examples of the super absorbent polymer particles include starch-based, cellulose-based, and synthetic polymer-based particles, and starch-acrylic acid (salt) graft copolymers, saponified starch-acrylonitrile copolymers, crosslinked sodium carboxymethylcellulose, and acrylic acid (salt) polymers can be used. As the shape of the super absorbent polymer particles, particulate materials which are usually used are preferable, but other shapes can also be used.

The super absorbent polymer particles having a water absorption rate of 70 seconds or less, particularly 40 seconds or less, are suitably used. If the water absorption rate is too slow, so-called returning, in which the liquid fed into the absorber 56 returns to the outside of the absorber 56, is likely to occur.

As the super absorbent polymer particles, those having a gel strength of 1000 Pa or more are suitably used. Thereby, even when the absorber 56 is bulky, it is possible to effectively suppress stickiness after liquid absorption.

The basis weight of the super absorbent polymer particles can be appropriately determined according to the absorption amount required for the use of the absorber 56. Therefore, although it cannot be said unconditionally, the basis weight can be 50 to 350 g/m$^2$. When the basis weight of the polymer is less than 50 g/m$^2$, it is difficult to ensure the absorption amount. When it exceeds 350 g/m$^2$, the effect is saturated.

If necessary, the super absorbent polymer particles can adjust a spraying density or a spraying amount in the planar direction of the absorber 56. For example, it is possible to increase the spraying amount in an excretory site of liquid compared to the other sites. When considering the difference between men and women, it is possible to increase the spray density (amount) on the front side for men and to increase the spray density (amount) at the center for women. Further, a portion without polymer can be provided locally (for example, in a spot shape) in the planar direction of the absorber 56.

(Wrapping Sheet)

When the wrapping sheet 58 is used, tissue paper, particularly crepe paper, a nonwoven fabric, a polyethylene laminated nonwoven fabric, a sheet with small openings can be used as the material. However, it is desirable that the sheet from which the super absorbent polymer particles do not come off be used. When a nonwoven fabric is used in place of crepe paper, a hydrophilic SMS nonwoven fabric (SMS, SSMMS, etc.) is particularly suitable, and polypropylene, polyethylene/polypropylene composite material, and the like can be used as the material. The basis weight is desirably 5 to 40 g/m$^2$, particularly desirably 10 to 30 g/m$^2$.

The wrapping mode of the wrapping sheet 58 can be appropriately determined. However, from the viewpoints of ease of manufacturing and prevention of leakage of highly absorbent polymer particles from the front and back end edges, it is preferable that the wrapping sheet 58 be wound around in a cylindrical shape so as to surround the front and back surfaces and both side surfaces of the absorber 56, the front and back edge portions are protruded from the front and back of the absorber 56, and an overlapping portion of the wound sheet and the protruding portions be joined by a joining means such as a hot melt adhesive and material welding.

(Indicator)

On the absorber 56 side of the liquid impervious sheet 11, it is possible to provide an indicator 80 which changes color by contact with a liquid content of excrement. The indicator 80 includes a sheet-like member that contains a coloring agent which indicates a color reaction by contact with a liquid content of excrement and/or a coloring agent which indicates a color reaction by detecting the pH in moisture, an ink or an adhesive containing other agents that indicate a reaction in which coloration disappears by reaction with a body fluid, a reaction blurred or disappeared since a coloring agent is dissolved (dispersed) by urine, and other visual changes, or an agent (indicator reaction means) that indicates a visual change by contact with moisture or a body fluid. For example, as a coloring agent that indicates a color reaction by contact with moisture such as a body fluid, the color agent can be used which contains a water-soluble, water-decomposable dye or a leuco dye and a developer such as a phenolic compound for coloring the leuco dye, acidic substances, or an electron accepting substance.

The color appearing due to coloration is not particularly limited, but when it is the same color as the outer surface of a diaper (normally white), it is difficult to recognize the coloration. Therefore, it is suitable to use a color of coloration different from that of the outer surface of a diaper.

Figure 2:
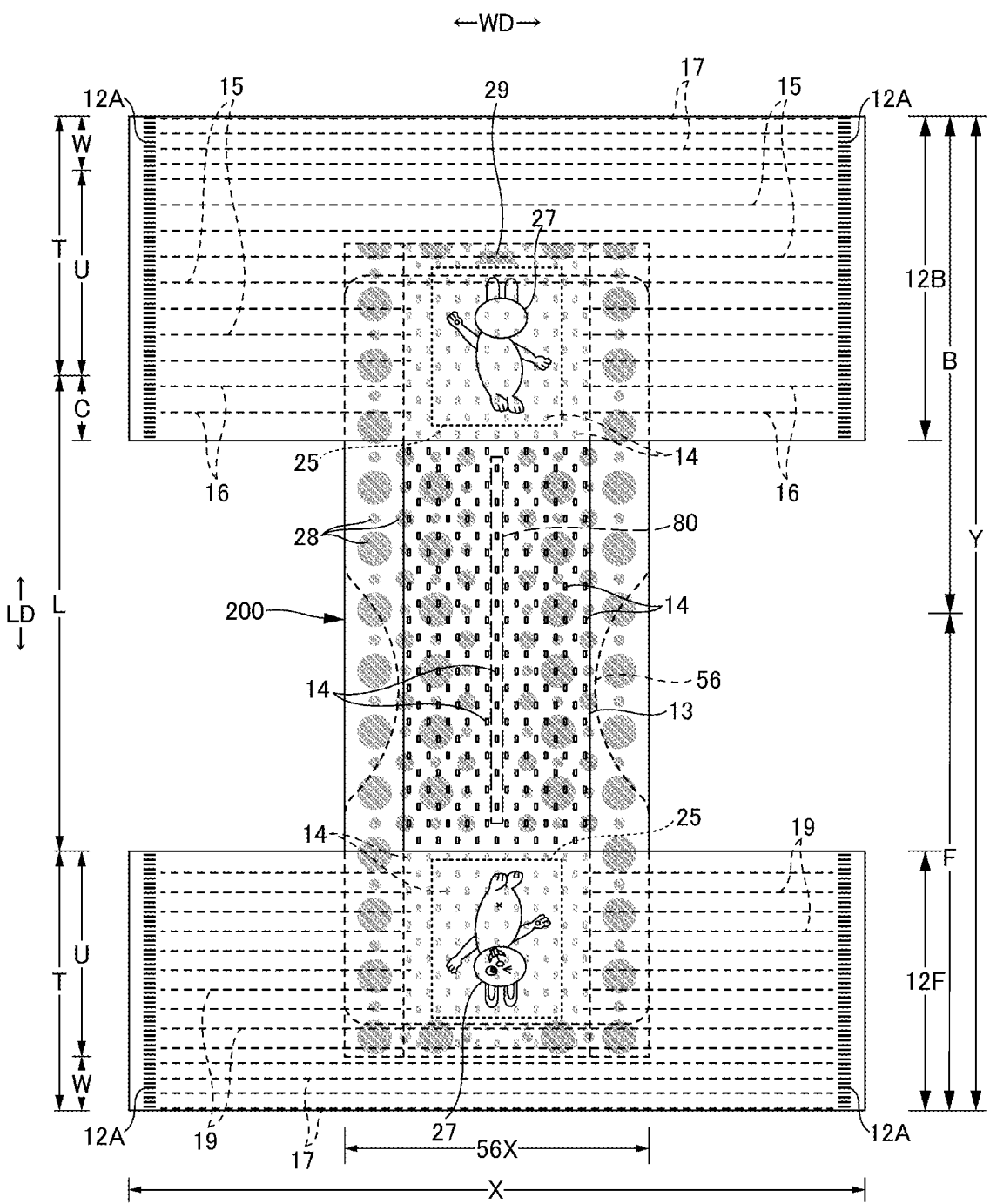
FIG. 2 is a plan view of an outer surface of an underpants-type disposable diaper in a spread state.

As illustrated in FIGS. 2 and 3, the indicator 80 including the above-described ink or adhesive is applied to a predetermined application region. Note that the indicator 80 illustrated in FIGS. 2 and 3 shows an application region of the above-described ink or adhesive. This region is preferably included in a disposition range of the absorber 56, is located at the center in the width direction, and has a width of about 0.2 to 5 cm, preferably about 0.4 to 2 cm and a length of 20 to 70% of the maximum length L of a diaper. Contact with excrement absorbed by the absorber 56 is efficiently performed in this region. The indicator 80 is desirably formed by applying an ink or an adhesive included in the indicator 80 between a back surface of the absorber 56 and the liquid impervious sheet 11, specifically on a side surface of the absorber 56 of the liquid impervious sheet 11 or an inner surface or outer surface of the wrapping sheet 58. The application pattern is not particularly limited, and it may be a band shape as illustrated in FIG. 7, or it may be applied in a pattern of a plane shape or other figures, in addition to a pattern with a large number of streaks. It is preferable that in the case of a belt-shaped pattern, the application width be 2 to 5 mm, and in the case of the pattern with a large number of streaks, the application width per streak is 1 to 2 mm, and about 2 to 4 strips are arranged at intervals of about 0.5 to 1.5 mm. It is obviously possible to separately manufacture a sheet on which the indicator 80 is formed and incorporate the sheet-like indicator 80 in a diaper. The indicator 80 is preferably disposed at a distance of 5 mm or more, particularly 10 mm or more, from decorative printing to be described later, since its discoloration is easily found.

When the indicator 80 is composed of an ink, the component of the indicator 80 is an ink in which a coloring agent is added. When the indicator 80 is composed of an adhesive, the component of the indicator 80 is an adhesive in which a water-insoluble polymer made of a resin and the like and a coloring agent are added to a water soluble polymer or a hydrophilic polymer. Specifically, in the case of being composed of an adhesive, a water-soluble polymer including a polyethylene glycol with molecular weight of 100 to 500, polyvinylpyrrolidone/vinyl acetate copolymer, and a water-soluble polyester, a water insoluble component of a highly polar tackifier resin and a plasticizer, and a coloring agent which indicates the degree of acidity/alkalinity (pH) of a liquid to be contacted by discoloration are included.

When the indicator 80 is made of an adhesive, various known adhesives can be used as the adhesive. As an example thereof, the case of using a hot melt adhesive will be described in detail. By using a hot melt adhesive containing a coloring agent as the indicator 80, it is possible to prevent diffusion and leaching of the coloring agent and the like. Further, compared to the case where a sheet-like indicator is provided, since it can be easily carried out in manufacturing line, it is possible to drastically reduce work process for attaching the indicator.

On the other hand, when the indicator 80 made of a sheet-like member is used, the sheet-like member is disposed between the liquid impervious sheet 11 and the absorber 56, specifically between the absorber 56 and the inner surface of the wrapping sheet 58 or between the back surface of the wrapping sheet 58 and the liquid impervious sheet 11. Note that when this sheet-like indicator 80 is used, the number of members is increased as compared with the case where the liquid indicator 80 is applied, but only the necessary amount can be easily used at the necessary sites, and the cost can be reduced by reducing the use area of the sheet-like member including an indicator reaction means.

(Outer Member)

The outer members 12F and 12B include the front side outer member 12F disposed in the front body F and the back side outer member 12B disposed in the back body B. The front side outer member 12F and the back side outer member 12B are not continuous on the crotch side but are separately provided in the front-back direction LD. The separation distance 12d can be, for example, about 150 to 250 mm The outer members 12F and 12B have lower torso portions which are ranges in the front-back direction, corresponding to the lower torso region T. In the present embodiment, the front side outer member 12F does not have a portion corresponding to the intermediate region L, but the back side outer member 12B has a gluteal cover portion C extending from the lower torso region T to the intermediate region L side. Although not illustrated, the front side outer member 12F may also be provided with an inguinal cover portion extending from the lower torso region T toward the intermediate region L side; even though the inguinal cover portion is provided, a gluteal cover portion may not be provided; or both the front side outer member 12F and the back side outer member 12B are not necessarily provided with a portion corresponding to the intermediate region L. Further, in the illustrated embodiment, the lower edge of the gluteal cover portion C is formed in a straight line along the width direction WD similarly to the lower edge of the front side outer member 12F. However, the lower edge of the gluteal cover portion C may be formed in a curved line such that the outer ends of the lower edge in the width direction are closing toward the waist opening.

As illustrated in FIGS. 4 and 5, the outer members 12F and 12B are formed by joining the outer sheet layer 12S and the inner sheet layer 12H by a joining means such as a hot melt adhesive or welding. A sheet material forming the outer sheet layer 12S and a sheet material forming the inner sheet layer 12H may be a common sheet material as in the embodiment of FIG. 5 or may be individual sheet materials. That is, in the former case, each of the inner sheet layer 12H and the outer sheet layer 12S is formed by the inner portion and the outer portion of one sheet material folded back at the edge of the waist opening WO (which may be a crotch side edge). The former structure has an advantage that the inner sheet layer 12H and the outer sheet layer 12S are not easily displaced when those are laminated. The latter structure has an advantage that the number of materials of the sheet material can be reduced.

A sheet material used for the outer sheet layer 12S and the inner sheet layer 12H can be used without particular limitation, but a nonwoven fabric is preferable, and for example, a nonwoven fabric composed of synthetic fibers such as olefin such as polyethylene and polypropylene, polyester, polyamide, and a nonwoven fabric composed of a mixed fiber, a composite fiber, or the like in which two or more of the above are used can be used. Further, the nonwoven fabric may be manufactured by any processing. Examples of the processing method include known methods such as a spun lace method, a spunbond method, a thermal bond method, a melt blown method, a needle punch method, an air-through method, and a point bond method. When a nonwoven fabric is used, its basis weight is preferably about 10 to 30 g/m$^2$.

Further, the total basis weight of the outer members 12F and 12B is preferably about 20 to 60 g/m$^2$.

(Stretchable Region/Non-stretchable Region)

The elongated elastic members 15 to 19 such as rubber threads or the like are provided between the outer sheet layer 12S and the inner sheet layer 12H to improve the fitting to the lower torso of a wearer on the outer members 12F and 12B. A stretchable region, which is elastically stretchable in the width direction WD with the elasticity of the elastic members, is formed. In this stretchable region, in the state of natural length, the outer sheet layer 12S and the inner sheet layer 12H contract as the elastic members contract, and wrinkles or folds are formed. When the stretchable region is stretched in the longitudinal direction of the elastic member, the outer sheet layer 12S and the inner sheet layer 12H can be stretched to a predetermined stretch rate at which the outer sheet layer 12S and the inner sheet layer 12H stretch without wrinkle. As the elastic members 15 to 19, synthetic rubber may be used, and also natural rubber may be used.

For bonding the outer sheet layer 12S and the inner sheet layer 12H in the outer members 12F and 12B and fixing the elastic members 15 to 19 sandwiched therebetween, at least one of a hot melt adhesive by various application methods and a fixing means by material welding such as heat seal or ultrasonic seal can be used. Since the flexibility is impaired when the whole outer members 12F and 12B are firmly fixed, it is preferable that the area other than the bonded portions of the elastic members 15 to 19 be not bonded or be weakly bonded. In the illustrated embodiment, a hot-melt adhesive is applied only to the outer peripheral surfaces of the elastic members 15 to 19 by an application means such as a comb gun or a SureWrap nozzle and is sandwiched between both the sheet layers 12S and 12H, whereby the elastic members 15 to 19 are fixed to both the sheet layers 12S and 12H, and the both sheet layers 12S and 12H are fixed by using only the hot melt adhesive applied to the outer peripheral surfaces of the elastic members 15 to 19. The elastic members 15 to 19 can be fixed to the outer sheet layer 12S and the inner sheet layer 12H only at both end portions in a stretchable direction in the stretchable region.

More specifically, between the outer sheet layer 12S and the inner sheet layer 12H in the waist portion W of the outer members 12F and 12B, a plurality of the waist portion elastic members 17 are attached at intervals in an up-down direction so as to extend in the whole width direction WD. Among the waist portion elastic members 17, one or a plurality of the waist portion elastic members 17 disposed in a region adjacent to the under-waist portion U may overlap with the inner member 200 or may be provided on both sides in the width direction except for the central portion in the width direction overlapping with the inner member 200. As these waist portion elastic members 17, about three to twenty two rubber threads having a fineness of about 155 to 1880 dtex, particularly about 470 to 1240 dtex (in the case of synthetic rubber), (a cross-sectional area is about 0.05 to 1.5 mm$^2$, particularly about 0.1 to 1.0 mm$^2$ in the case of natural rubber) are preferably provided at an interval of 4 to 12 mm, and accordingly a stretch rate of the width direction WD of the waist portion W is preferably about 150 to 400%, particularly about 220 to 320%. In addition, it is unnecessary to use the waist portion elastic members 17 having the same thickness in the whole front-back direction LD in the waist portion W or to set to the same stretch rate. For example, at an upper portion and a lower portion of the waist portion W, the elastic member 17 may be different in thickness and the stretch rate.

Between the outer sheet layer 12S and the inner sheet layer 12H in the under-waist portion U of the outer members 12F and 12B, a plurality of under-waist portion elastic members 15 and 19 formed of elongated elastic members are attached at intervals in the up-down direction.

As the under-waist portion elastic members 15 and 19, five to thirty rubber threads each having a fineness of about 155 to 1880 dtex, particularly about 470 to 1240 dtex (in the case of synthetic rubber), (a cross-sectional area is about 0.05 to 1.5 mm$^2$, particularly about 0.1 to 1.0 mm$^2$ in the case of natural rubber) are preferably provided at a intervals of 1 to 15 mm, particularly 3 to 8 mm, and accordingly a stretch rate of the width direction WD of the under-waist portion U is preferably about 200 to 350%, particularly about 240 to 300%.

Further, between the outer sheet layer 12S and the inner sheet layer 12H in the gluteal cover portion C of the back side outer members 12B, a plurality of cover portion elastic members 16 formed of elongated elastic members are attached at intervals in the up-down direction.

As the cover portion elastic members 16, about two to ten rubber threads having a fineness of about 155 to 1880 dtex, particularly about 470 to 1240 dtex (in the case of synthetic rubber), (a cross-sectional area is about 0.05 to 1.5 mm$^2$, particularly about 0.1 to 1.0 mm$^2$ in the case of natural rubber) are preferably provided at intervals of 5 to 40 mm, particularly 5 to 20 mm, and accordingly a stretch rate of the width direction WD of the cover portion is preferably about 150 to 300%, particularly about 180 to 260%.

Similarly, in the case where an inguinal cover portion is provided on the front side outer member 12F, it is possible to provide the cover portion elastic members.

Like the under-waist portion U and the gluteal cover portion C in the illustrated embodiment, when the elastic members 15, 16, and 19 are provided in the range in the front-back direction having the absorber 56, in order to prevent a part of or the whole of the absorber 56 from contracting in the width direction WD, a middle in the width direction (preferably including the entire inner and outer joined portion 201) including a part or the whole of the portion overlapping with the absorber 56 in the width direction WD is set to a non-stretchable region A1, and the both sides in the width direction thereof are set to stretchable regions A2. It is preferable that the waist portion W be formed as the stretchable region A2 throughout the whole width direction WD. However, similarly to the under-waist portion U, the non-stretchable region A1 may be provided in the middle in the width direction.

The stretchable region A2 and the non-stretchable region A1 are provided with the elastic members 15 to 17 and 19 between the inner sheet layer 12H and the outer sheet layer 12S. The elastic members 15, 16, and 19 are fixed at least at both end portions in the stretchable direction in the stretchable region A2 with a hot melt adhesive and are not fixed in the region to be the non-stretchable region A1. In a region to be the non-stretchable region A1, the elastic members 15, 16, and 19 are cut by pressing and heating at one position at the middle in the width direction, or nearly the entire elastic members 15, 16, and 19 are finely cut by applying pressure and heating. While leaving the elasticity in the stretchable region A2, the elasticity in the non-stretchable region A1 is killed. In the former case, as illustrated in FIG. 4, in the non-stretchable region A1, residual portions continued from the elastic members 15, 16, and 19 of the stretchable regions A2 remain between the outer sheet layer 12S and the inner sheet layer 12H as idle elastic members 18 in a state where each idle elastic member 18 is independently contracted to a natural length. In the latter case, although not illustrated, residual portions continued from the elastic members 15, 16, and 19 of the stretchable regions A2 and cut pieces of the elastic members separated from the elastic members 15, 16, and 19 of the both stretchable regions A2 remain between the outer sheet layer 12S and the inner sheet layer 12H as idle elastic members in a state where each idle elastic member is independently contracted to natural length.

(Cover Nonwoven Fabric)

In the outer member separated-type underparts-type disposable diaper, the inner member 200 is exposed between the front side outer member 12F and the back side outer member 12B. Therefore, in order that the liquid impervious sheet 11 is not exposed on a back surface of the inner member 200, the cover nonwoven fabric 13 that covers the back surface of the inner member 200 from between the front side outer member 12F and the inner member 200 to between the back side outer member 12B and the inner member 200 is provided.

The cover nonwoven fabric 13 can be fixed to the liquid impervious sheet 11 and the gather nonwoven fabric 62 with a hot melt adhesive, and the application pattern of the hot melt adhesive is preferably a planar pattern such as a curtain, a summit, and a spiral. The fixing region of the cover nonwoven fabric 13 is the whole front-back direction and the whole width direction of the cover nonwoven fabric 13, and a part thereof may be non-fixed. For example, when both the end portions in the width direction of the cover nonwoven fabric 13 are not fixed, there is an advantage that even in a state in which the side portions of the absorber 56 are somewhat contracted due to the influence of the side gathers 60, the cover nonwoven fabric 13 is not easily affected thereby, and wrinkles and folds are not easily formed on the cover nonwoven fabric 13. In this case, the width of the non-fixed portion at each of both the end portions in the width direction of the cover nonwoven fabric 13 may be appropriately determined, but it may be, for example, 3 to 10 mm, preferably 5 to 8 mm Characteristically, as the cover nonwoven fabric 13, a perforated nonwoven fabric is used in which a large number of holes 14 penetrating the front surface and the back surface are provided at intervals. The kind of fiber of the perforated nonwoven fabric and the method for binding the fibers (for the entanglement) are not particularly limited and the kind and method similar to those of the outer sheet can be appropriately selected, but it is desirable to use an air-through nonwoven fabric. In such a case, the basis weight is preferably 20 to 40 g/m$^2$, and the thickness is preferably 0.2 to 1.0 mm.

Figure 8:
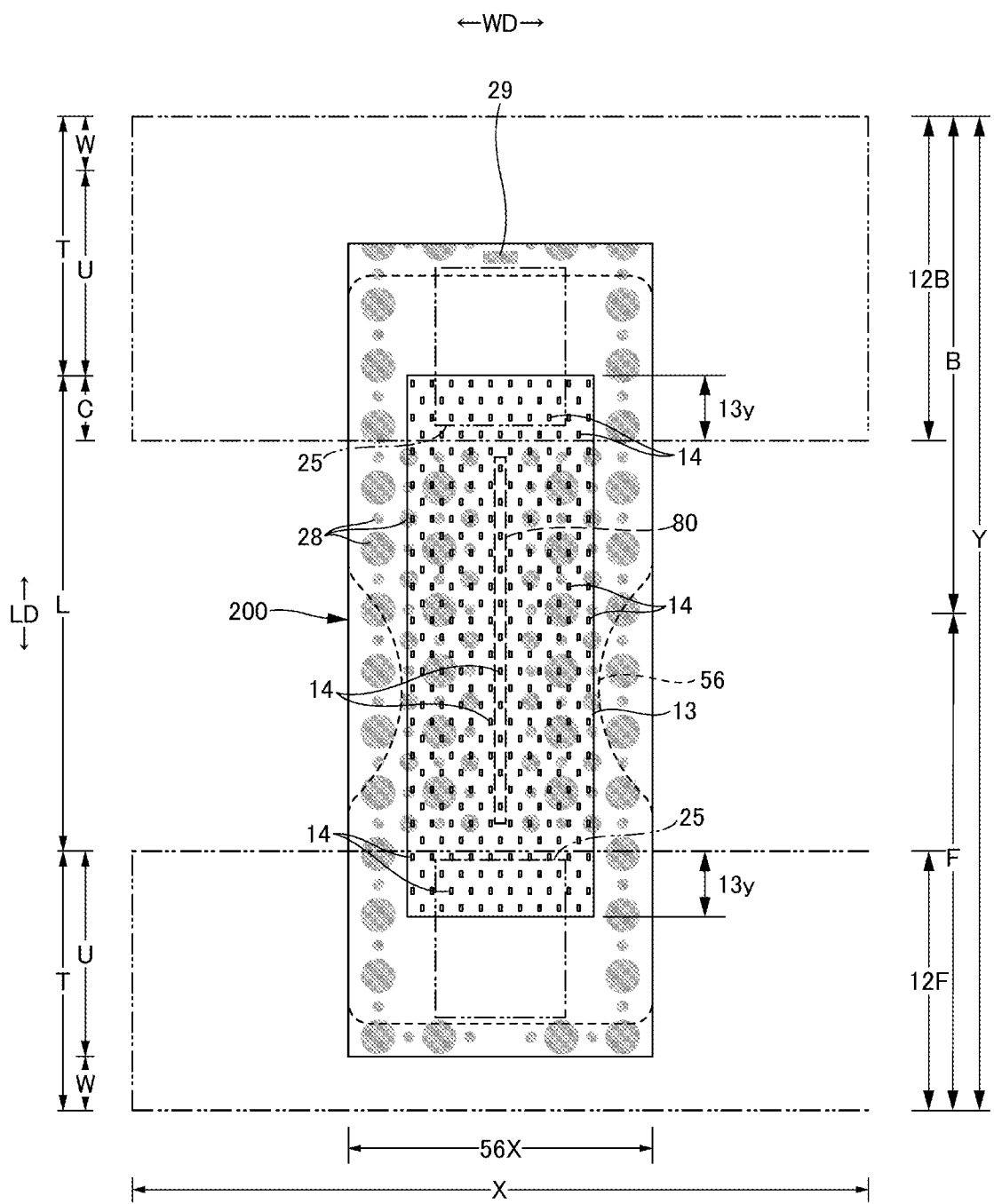
FIG. 8 is a plan view of an outer surface of an inner member in a spread state together with an outline of an outer member.

The range of the cover nonwoven fabric 13 in the front-back direction is not particularly limited as long as it has the portions overlapping with the front side outer member 12F and the back side outer member 12B. As illustrated in FIGS. 2, 5, 7, 9, and 10, the range of the cover nonwoven fabric 13 may extend in the front-back direction LD entirely from a front end to a back end of the inner member 200. As illustrated in FIG. 8, it may extend in the front-back direction LD from an intermediate position in the front-back direction of a region where the front side outer member 12F and the inner member 200 overlap each other to an intermediate position in the front-back direction of a region where the back side outer member 12B and the inner member 200 overlap each other. In the latter case, a length 13y in the front-back direction of the portion where the cover nonwoven fabric 13 and the front side outer member 12F overlap each other and the length 13y in the front-back direction of the portion where the cover nonwoven fabric 13 and the back side outer member 12B overlap each other can be appropriately determined, but in the usual case, they can be each about 20 to 40 mm.

The range in the width direction of the cover nonwoven fabric 13 is a range that can hide an exposed portion on a back surface of the liquid impervious sheet 11. For this reason, in the illustrated embodiment, since the liquid impervious sheet 11 is exposed between the base ends of the left and right side gathers 60, the cover nonwoven fabric 13 is provided so as to cover a width direction range from at least a back surface side of the base portion of one side gather 60 to a back surface side of the base portion of the other side gather 60. Accordingly, the liquid impervious sheet 11 can be hidden with the cover nonwoven fabric 13 and the gather nonwoven fabrics 62 of the side gathers 60, and when viewed on the outer surface, the holes 14 at both end portions of the cover nonwoven fabric 13 in the width direction WD are not hidden by the gather nonwoven fabric 62. Further, when the side edges of the cover nonwoven fabric 13 are located at positions same as the side edges of a narrowest part of the absorber 56 in the width direction (the full width of the absorber when the narrowing portion 56N is not provided), (the maximum width of the narrowest portion of the narrowing portion 56N when the narrowing portion 56N is provided), or located at positions on the center side in the width direction with respect to the side edges of the narrowest part, since the cover nonwoven fabric 13 is positioned such that the whole cover nonwoven fabric 13 overlaps with the absorber 56, that is, the cover nonwoven fabric 20 is positioned only in a portion where rigidity is high and wrinkles and folds are unlikely to occur, both the side portions of the cover nonwoven fabric 13 are unlikely to contract in the front-back direction LD, and wrinkles are unlikely to be formed on the both side portions of the cover nonwoven fabric 13, and collapse of the holes 14 is unlikely to occur. Further, even if the both end portions in the width direction of the cover nonwoven fabric 13 do not cover a back surface side of the base portions of the side gathers 60, and the gather nonwoven fabrics 62 cover the back surface side of both end portions in the width direction of the cover nonwoven fabric 13, the liquid impervious sheet 11 can be concealed with the cover nonwoven fabric 13 and the gather nonwoven fabric 62. In that case, when the total luminous transmittance of the gather nonwoven fabric 62 is 60 to 90%, even in portions where the gather nonwoven fabrics 62 hide the cover nonwoven fabric 13, the holes 14 of the perforated nonwoven fabric are transparent and can be visually recognized sufficiently, and it can be recognized that a portion having the air-permeability-improving function extends to the side gathers 60. Consequently, the visual effect of the holes 14 is sufficiently exerted.

Figure 11:
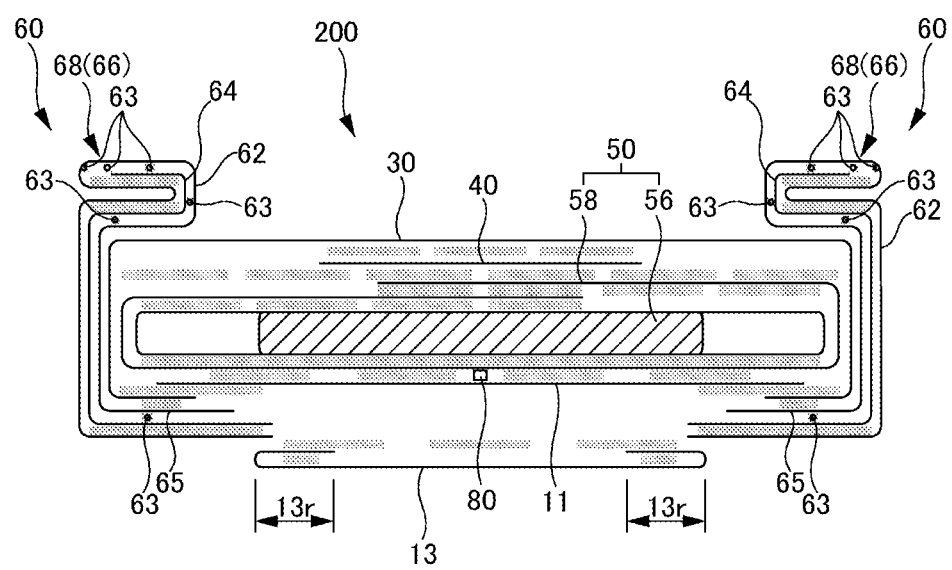
FIG. 11 is a cross-sectional view taken along line 2-2 in FIG. 1 according to another embodiment.

One preferred embodiment is that folded portions 13r are included at both the end portions in the width direction of the cover nonwoven fabric 13 in order to prevent wrinkles on both the side portions of the cover nonwoven fabric 13 and collapsing of the holes 14 as illustrated in FIG. 11. The folded width of the folded portion 13r is preferably 5 to 30 mm, particularly preferably 10 to 20 mm. In addition, even in the case of providing the folded portions 13r, it is preferable to provide non-fixed portions with respect to the inner member 200 at both the end portions in the width direction as described above. As a result, the stiffness of portions of the cover nonwoven fabric 13 is increased where contraction is likely to occur in the front-back direction LD, and wrinkling and collapse of the holes 14 are unlikely to occur. Whether or not to join the back surfaces of the folded cover nonwoven fabric 13 is arbitrary, but if at least at the fold portions (each having the range of about 3 to 8 mm in width), the back surfaces of the cover nonwoven fabric are not bonded each other with a hot melt adhesive or the like, there is an advantage that the side edges are rounded such that the texture is not rough. Further, since a nonwoven fabric is doubled in the folded portions 13r, when the liquid impervious sheet 11 and the gather nonwoven fabric 62 are fixed with a hot melt adhesive, even if a large amount of adhesive is applied to an intermediate portion in the width direction, the adhesive does not ooze out. In this manner, the adhesive strength of the end portions of the cover nonwoven fabric 13 in the width direction increases, and the flexibility can be further increased at the intermediate portion in the width direction by reducing the adhesive material.

In the cover nonwoven fabric 13, as long as a region where the holes 14 are formed extends from a portion overlapping with the front side outer member 12F to a portion overlapping with the back side outer member 12B, there may be a region without the holes 14 partly in the front-back direction LD. However, it is desirable to provide the holes 14 throughout totally in the front-back direction in consideration of the effect of improving air permeability. On the other hand, in the embodiment in which both the end portions of the cover nonwoven fabric 13 in the width direction WD have regions without the holes 14, when each hole 14 is opened by a method other than punching with a cutter, as will be described later, fibers at the edge of the hole 14 are retracted outside or in the vertical direction, and the edge portion of the hole 14 bends-up, and the thickness of a perforated region becomes thicker than that of a non-perforated region. Therefore, when a material of the cover nonwoven fabric 13 is stored in a rolled state, the non-perforated regions are loosely wound, and wrinkles and folds may be formed in the non-perforated regions at both the sides. Therefore, it is desirable that the holes 14 be formed in the whole width direction WD as in the illustrated embodiment. By forming the holes in the cover nonwoven fabric 13 in the manufacturing process of a diaper, materials without holes can be used, and positions of the holes can be arbitrarily controlled. However, by introducing a device for forming the holes, the whole of a manufacturing facility becomes large, and a burden of cost and maintenance increases. In addition, it is difficult to adjust the hole shape and softness in a manufacturing line at high speed. Therefore, it is preferable to manufacture a diaper using a material in which the holes are formed throughout totally in the front-back direction and the width direction.

Figure 17:
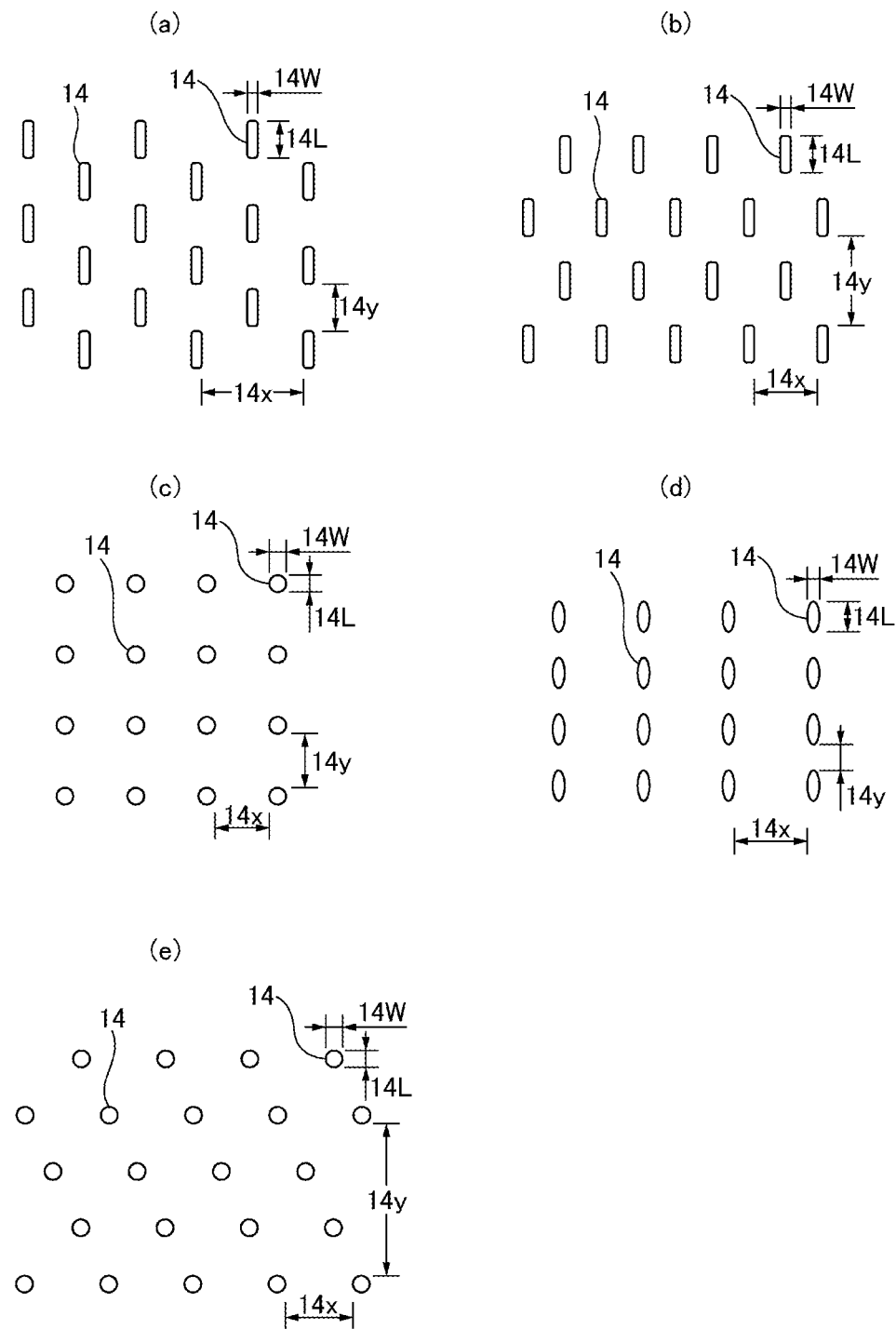
FIG. 17 is an enlarged plan view of a main part of a perforated nonwoven fabric.

A planar shape (opening shape) of each hole 14 can be appropriately determined. It can have an arbitrary shape such as an elongated hole shape as illustrated in FIGS. 17(a) and 17(b), a perfect circle as illustrated in FIGS. 17(c) and 17(e), an ellipse as illustrated in FIG. 17(d), a polygon such as a triangle, a rectangle, and a rhombus, a star shape, a cloud shape and the like. Although the dimensions of the individual holes 14 are not particularly limited, but the dimension in the front-back direction (maximum dimension in the front-back direction LD) 14L is preferably is 0.4 to 1.8 mm, particularly preferably 0.8 to 1.3 mm, and the width direction dimension (the maximum dimension in the width direction WD) 14W is preferably 0.3 to 1.5 mm, particularly preferably 0.5 to 1.0 mm. In the case where the shape of the hole 14 is long in one direction like a long hole shape, an elliptic shape, a rectangular shape, and a diamond shape, the maximum dimension in the longitudinal direction is preferably 2.5 times or less the maximum dimension in the direction orthogonal thereto. Further, when the shape of the hole 14 is long in one direction, it is desirable that the longitudinal direction of the hole 14 be the front-back direction LD, but it may be the width direction WD or the oblique direction.

An area and an area rate of the individual holes 14 may be appropriately determined, but the area is preferably about 0.2 to 2.5 mm$^2$ (particularly about 0.5 to 1.5 mm$^2$), and the area rate is about 0.5 to 5.0% (particularly about 1.0 to 2.5%).

Although the planar arrangement of the holes 14 can be appropriately determined, a regularly repeated plane arrangement is preferred. In addition to the regularly repeated plane arrangement, such as an oblique lattice shape as illustrated in FIG. 17(a), a hexagonal lattice shape (also referred to as a staggered shape) as illustrated in FIG. 17(b), a square lattice shape as illustrated in FIG. 17(c), a rectangular lattice shape as illustrated in FIG. 17(d), and a parallel lattice shape as illustrated in FIG. 17(e) (as illustrated in the drawing, two groups of many parallel oblique direction rows are provided so as to cross each other) (including those inclined at an angle of less than 90° with respect to the front-back direction LD), a group of the holes 14 (the group may be regularly or irregularly arranged, and may be a pattern or a letter shape) can be regularly repeated.

An interval 14y of the two adjacent holes in the front-back direction and an interval 14x of the two adjacent holes in the width direction can be appropriately determined, but in consideration of air permeability, it is desirable to set each within the range of 0.5 to 8 mm, particularly 1 to 5 mm, and the front-back direction interval 14y and the width direction interval 14x are preferably set to be within the range of 1 to 5 mm on average. In particular, as illustrated in FIG. 17(d), when the shape of the hole 14 is elongated in the front-back direction LD, a row of the holes 14, which are aligned in the front-back direction LD at the intervals 14y in the front-back direction narrower than the dimension 14L in the front-back direction of the hole 14, is repeated at a predetermined interval in the width direction WD, and the interval 14x of the two adjacent holes in the width direction is wider than the dimension 14L in the front-back direction of the hole 14 (more preferably three times or more the dimension 14W in the width direction of the hole 14), it is preferable since softness and bulkiness are not impaired while remarkably improving the air permeability, and also there is no decrease in the tensile strength of the sheet in the front-back direction which is important in manufacturing.

Figure 14:
FIG. 14(a) is a perspective view of a hole of a perforated nonwoven fabric.
FIG. 14(b) is a plan view thereof.
FIG. 14(c) is a cross-sectional view taken along line 1-1.
Figure 14:
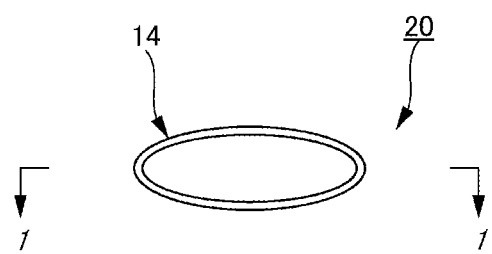
Figure 14:
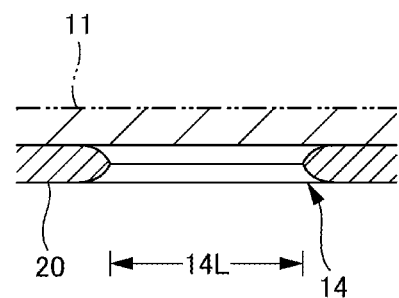
Figure 15:
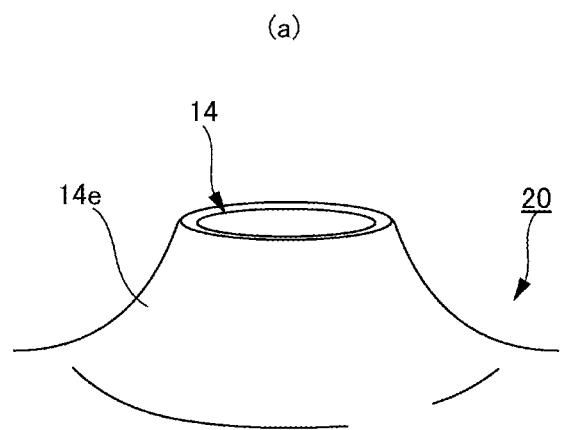
FIG. 15(a) is a perspective view of a hole of a perforated nonwoven fabric.
FIG. 15(b) is a plan view thereof, and FIG. 15(c) a cross-sectional view taken along line 1-1.
Figure 15:
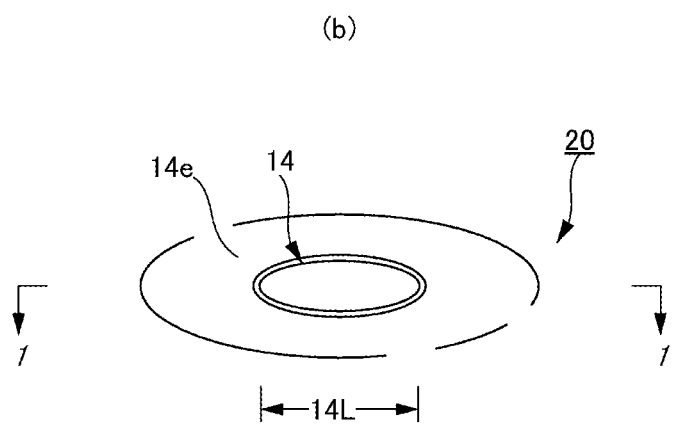
Figure 15:
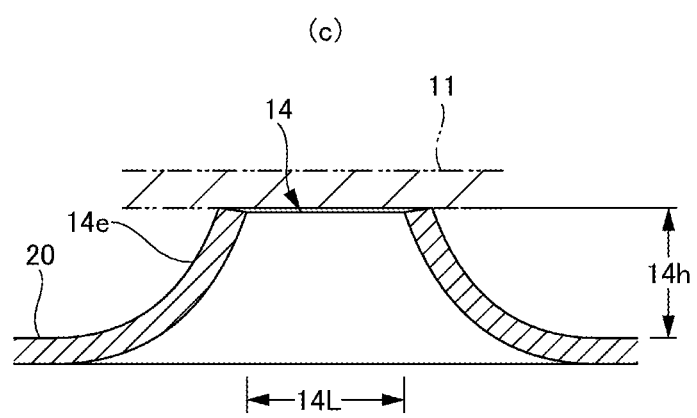
Figure 16:
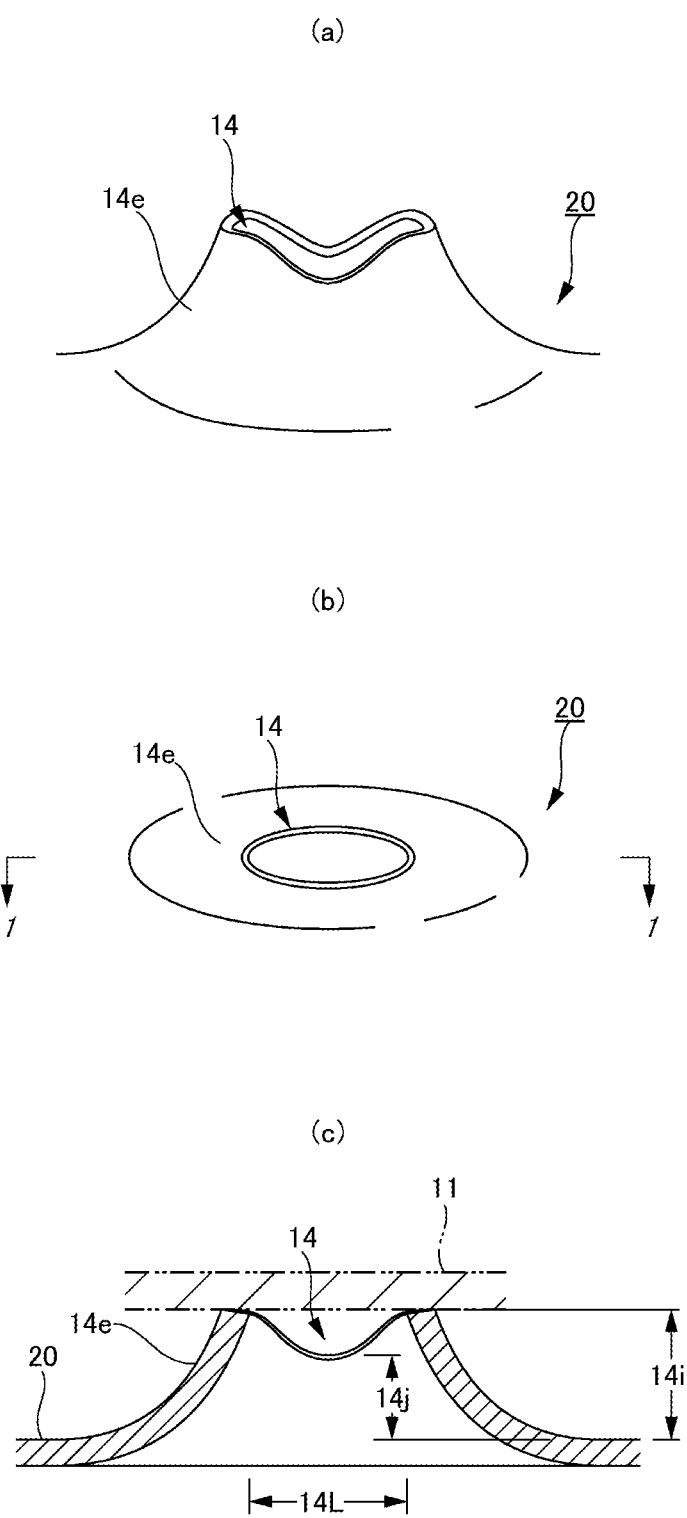
FIG. 16(a) is a perspective view of a hole of a perforated nonwoven fabric.
FIG. 16(b) is a plan view thereof.
FIG. 16(c) is a cross-sectional view taken along line 1-1.

The first to third embodiments can be applied to the sectional shape of the hole 14. In the first embodiment, the thickness of a nonwoven fabric decreases from a periphery of the hole 14 toward an edge of the hole 14, and the edge of the hole 14 is positioned in the middle in the thickness direction of the nonwoven fabric as illustrated in FIG. 14. In the second embodiment, an edge portion 14e of the hole 14 is bent-up toward a front surface side, and the bending-up height 14h is substantially uniform as illustrated in FIG. 15. In the third embodiment, the edge portion 14e of the hole 14 bends-up toward a front surface side, and the edge portion 14e includes a highest opposing portion having the highest bending-up height 14i; and a lowest opposing portion being orthogonal in the opposing direction to the highest opposing portion and having the lowest bending-up height 14j as illustrated in FIG. 16. From the viewpoint of air permeability, the second and third embodiments in which a portion including the holes 14 is thicker than the surroundings are desirable. In particular, the third embodiment is preferable since a gap formed by a difference in bending-up heights 14i and 14j in the edge portion 14e of the hole 14 contributes to improvement of air permeability. In the second and third embodiments, it is preferable that the bending-up heights 14g, 14h, and 14i (the apparent height measured by using an optical microscope in a state where a pressure is not applied) be about 0.2 to 1.2 mm, and the highest bending-up height 14i in the third embodiment is preferably about 1.1 to 1.4 times the lowest bending-up height 14j.

The hole 14 may be a punched hole whose edge portion is formed by cut ends of fibers and may be a non-punched hole (to have an edge portion with fibers having a high density) having almost no cut end of the fiber at the edge portion of the hole 14 and formed by inserting and pushing a pin among the fibers. The former is suited for the first embodiment, and the latter is suited for the second and third embodiments. For example, when the hole 14 having a long dimension in one direction is formed by inserting a pin, the fibers in the edge portion 14e of the hole 14 are retracted outside or in a vertical direction, the edge portion 14e of the hole 14 bends-up, and the bending-up height i of the opposing portion in the longitudinal direction of the hole 14 is higher than the bending-up height j of the opposing portion being orthogonal in the opposing direction to the longitudinal direction. In the second and third embodiments, the edge portion at a part where the edge portion 14e of the hole 14 is bent-up toward the surface may have a lower density of the fibers than those of surroundings in some cases, but it is preferable that it be equal to or higher than those of the surroundings. Further, it is desirable that the fibers at the edge portion of the hole 14 be fusion bonded to each other, but may not be fused.

(Regarding Total Luminous Transmittance of Outer Member)

When the front side outer member 12F and the back side outer member 12B have, at least at portions overlapping with the cover nonwoven fabric 13 and not having any elastic member, the total luminous transmittance of 50% or more (preferably 65% or more), it is preferable since even in portions hidden by the front side outer member 12F and the back side outer member 12B in the cover nonwoven fabric 13, the holes 14 of the perforated nonwoven fabric are transparent and can be visually recognized sufficiently, and therefore, it can be recognized that a portion having an air-permeability-improving function is provided not only a part between the front side outer member 12F and the back side outer member 12B, but also on both the front and back sides of the part, and the visual effect of the holes 14 can be sufficiently exerted. The total luminous transmittance of the outer members 12F and 12B is measured in a state where the outer sheet layer 12S and the inner sheet layer 12H are overlapped.

(Regarding Decorative Printing)

Decorative printing 27 and 28 (inner decorative printing 28) such as characters and patterns can be provided on the liquid impervious sheet 11 so as to be visible on an outer surface of a product. When such inner decorative printing 28 is provided, if the inner decorative printing 28 and the holes 14 of at least a part of the cover nonwoven fabric 13 are arranged to overlap with each other, it is preferable since the holes 14 of a perforated nonwoven fabric emerge against a background of the inner decorative printing 28, and the holes 14 can be easily seen through the outer surface. To prevent positional deviation of the inner decorative printing 28 during manufacturing, it is also possible to print a so-called registration mark 29 on the liquid impervious sheet 11.

On the other hand, since the inner decorative printing 28 is covered with the perforated nonwoven fabric, the appearance as decoration may be deteriorated. Therefore, regarding the decoration emphasizing the appearance, it is desirable that an outer decorative sheet 25 having outer decorative printing 27 be provided on an outer side of the cover nonwoven fabric 13 at least in one of the region where the front side outer member 12F and the cover nonwoven fabric 13 overlap each other and the region where the back side outer member 12B and the cover nonwoven fabric 13 overlap each other. In this case, to make the holes 14 of the perforated nonwoven fabric transparent and possible to be visually recognized sufficiently even in the portions hidden by the front side outer member 12F and the back side outer member 12B in the cover nonwoven fabric 13, both the edges on the crotch side of both the outer decorative sheets 25 are preferably spaced apart by about 5 to 30 mm from an edge portion on the crotch side of the front side outer member 12F and from an edge portion on the crotch side of the back side outer member 12B. Additionally, each of the outer decorative sheets preferably has a width being narrower than that of the cover nonwoven fabric 13 such that both side edges of the outer decorative sheet 25 are spaced apart by about 5 to 30 mm from each of the both side edges of the cover nonwoven fabric 13.

As in the illustrated embodiment, the liquid impervious sheet 11 may have, at a region overlapping with the outer decorative sheet 25, the inner decorative printing 28, but preferably does not have, at the region, the inner decorative printing 28 (such that the outer decorative sheet 25 and the inner decorative printing 28 do not overlap). That is because even if a member with low visible light permeability is used for the outer decorative sheet 25, it can be prevented that the inner decorative printing 28 is partially hidden by the outer decorative sheet 25, and the appearance does not deteriorate. Further, the outer decorative sheet 25 may overlap with the registration mark 29. In that case, the outer decorative printing 27 and the registration mark 29 may overlap each other. However, it is preferable that a printing position of the outer decorative printing 27 and a position of the registration mark 29 are adjusted so as not to overlap, since the appearance deterioration of the outer decorative printing 27 due to overlapping viewing of the outer decorative printing 27 and the registration mark 29 can be prevented.

The type, shape, and size of the inner decorative printing 28 and the outer decorative printing 27 are not particularly limited. As the decorative printing 27 and 28, in addition to continuous decorative printing (refer to the inner decorative printing 28 of FIGS. 2, 7, and 8) composed of many elements such as characters (such as a size, a brand name, a manufacturer name, and a picture name) and pictures, which are regularly repeated in the front-back direction LD and the width direction WD, there is an intermittent decorative printing (refer to the outer decorative printing 27 of FIG. 2) arranged only on one or both of the front and back of a product, such as a product logo, a picture of a character, and a photograph. Either of the inner decorative printing 28 and the outer decorative printing 27 may be adopted. However, it should be noted as follows. The continuous decorative printing is a repetition of a large number of elements, and there is almost no influence on appearance even as a background of the perforated nonwoven fabric. On the other hand, when the intermittent decorative printing is covered with the perforated nonwoven fabric, there is a difference in appearance between the portions having the holes 14 and the other portions, and the intermittent decorative printing is partly hidden due to high concealing property of the edge portions of the holes 14. Consequently, the deterioration of appearance becomes remarkable. Therefore, it is preferable to distinguish a member having the inner decorative printing 28 and a member having the outer decorative printing 27, and apply the continuous decorative printing to the inner decorative printing 28 and the intermittent decorative printing to the outer decorative printing 27. Although the inner decorative printing 28 may be intermittent decorative printing, it is desirable that the inner decorative printing 28 does not have at least a complicated pattern.

The inner decorative printing 28 may be printed on either the front surface side or the back surface side of the liquid impervious sheet 11 or may be printed on both the front and back surfaces. Similarly, the outer decorative printing 27 may be printed on either the front surface side or the back surface side of the outer decorative sheet 25 or may be printed on both the front and back surfaces.

The base material of the outer decorative sheet 25 is not particularly limited as long as it is suited for printing, and paper such as crepe paper, a resin film, or the like can be used, for example. When the crepe paper is used, its thickness is preferably 100 to 150 μm, and the density is preferably 100 to 200 kg/m$^3$. Crepe paper having such thickness and density can be produced with a crepe ratio of around 10% at a basis weight of 10 g/m$^2$ or more. The density can be calculated from the basis weight and the thickness. Further, the crepe ratio is a value calculated by the equation; ((peripheral speed of Yankee dryer)−(peripheral speed of winding reel))/(peripheral speed of Yankee dryer)× 100(%). When the outer decorative sheet 25 is provided near an outer surface of a product, it is easy to see from the outside of the product. Therefore, as illustrated in the figure, the outer decorative sheet 25 is desirably provided adjacent to the inner surface of the outer sheet layer 12S between the outer sheet layer 12S and the inner sheet layer 12H, but it may be provided adjacent to an outer surface of the inner sheet layer 12H. Further, it may be provided between the outer member 12F, 12B and the inner member.

In the case of providing the indicator 80 which discolors in contact with the liquid content of excrement, the indicator 80 is preferably provided on the liquid impervious sheet 11 at a region not having the inner decorative printing 28 so as to be separated by 5 mm, particularly 10 mm or more, from the inner decorative printing 28. It is preferable that at least a part of the indicator 80 when provided, particularly in the case of a belts-shaped or streaks-like pattern extending in the front-back direction LD, at least one belt or streak be disposed so as to overlap with the holes 14 of the cover nonwoven fabric 13 at a plurality of places. For example, preferably, in the case where a plurality of rows of the holes 14 are provided as in FIGS. 17(a), 17(b), 17(c), and 17(d), at least one belt or streak in each of the strips-like or streaks-like patterns of the indicator 80 overlaps with the row of the holes 14. In addition, as in the parallel grid illustrated in FIG. 17(e), it is preferable that the strips and streaks of the indicator 80 be always arranged so as to overlap with the holes even if the belts and streaks are deviated somewhat due to camber of the material. As a result, a user can easily notice discoloration of the indicator 80 because of two kinds of visibility: not only by discoloration of the indicator 80 but also by the difference in color of the indicator 80 looking through the holes 14 and the indicator 80 visible through the nonwoven fabric. At this time, when the width per one belt or streak of the indicator 80 is twice or more the dimension 14W in the width direction of the hole 14 of the cover nonwoven fabric 13 and is narrower than the width direction interval 14x of the holes 14, the indicator 80 and the holes 14 are likely to overlap even if the positions are slightly deviated, and also it is preferable because the visibility of the indicator 80 in an overlapped state is remarkably improved. Incidentally, if the total luminous transmittance of the cover nonwoven fabric 13 (at a portion without the holes 14) is 60 to 90%, it is preferable since the difference between the color visible through the holes 14 and the color visible through the nonwoven fabric is increased, and the holes 14 are easily noticed.

(Inner and Outer Joined Portion)

The inner member 200 can be fixed to the outer members 12F and 12B by a joining means by material welding such as heat seal and ultrasonic seal and a hot melt adhesive. In the illustrated embodiment, the inner member 200 is fixed to the inner surfaces of the outer members 12F and 12B with a hot melt adhesive applied on a back surface of the inner member 200, that is, in this case, a back surface of the liquid impervious sheet 11, and the root portion 65 of the side gather 60. The inner and outer joined portions 201 for fixing the inner member 200 and the outer members 12F and 12B can be provided to almost entirely in the region where both are overlapped with each other, and for example, the inner and outer joined portion 201 can be provided in a portion excluding both end portions of the inner member 200 in the width direction.

Figure 9:
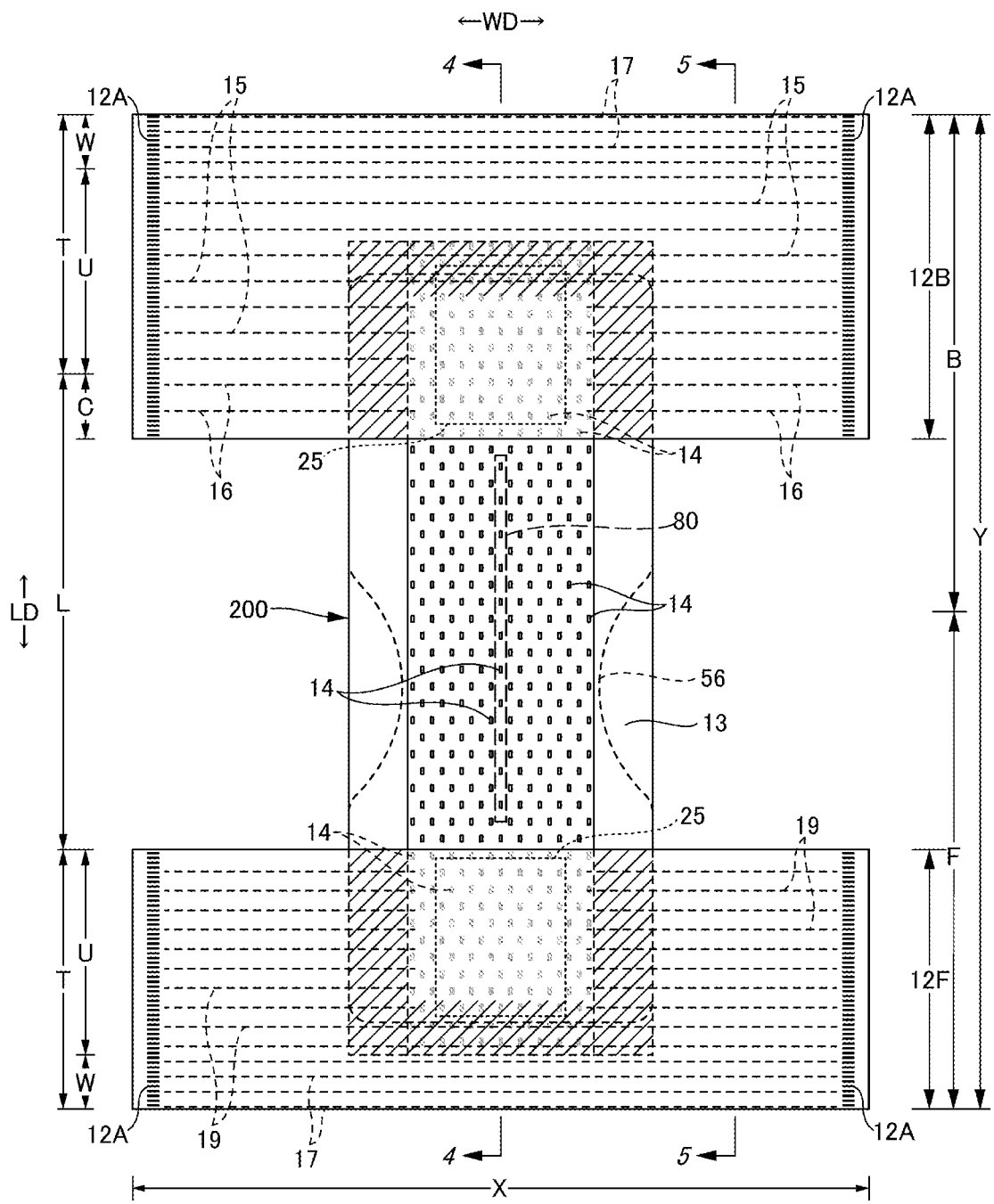
FIG. 9 is a plan view of an outer surface of an underpants-type disposable diaper in a spread state.
Figure 10:
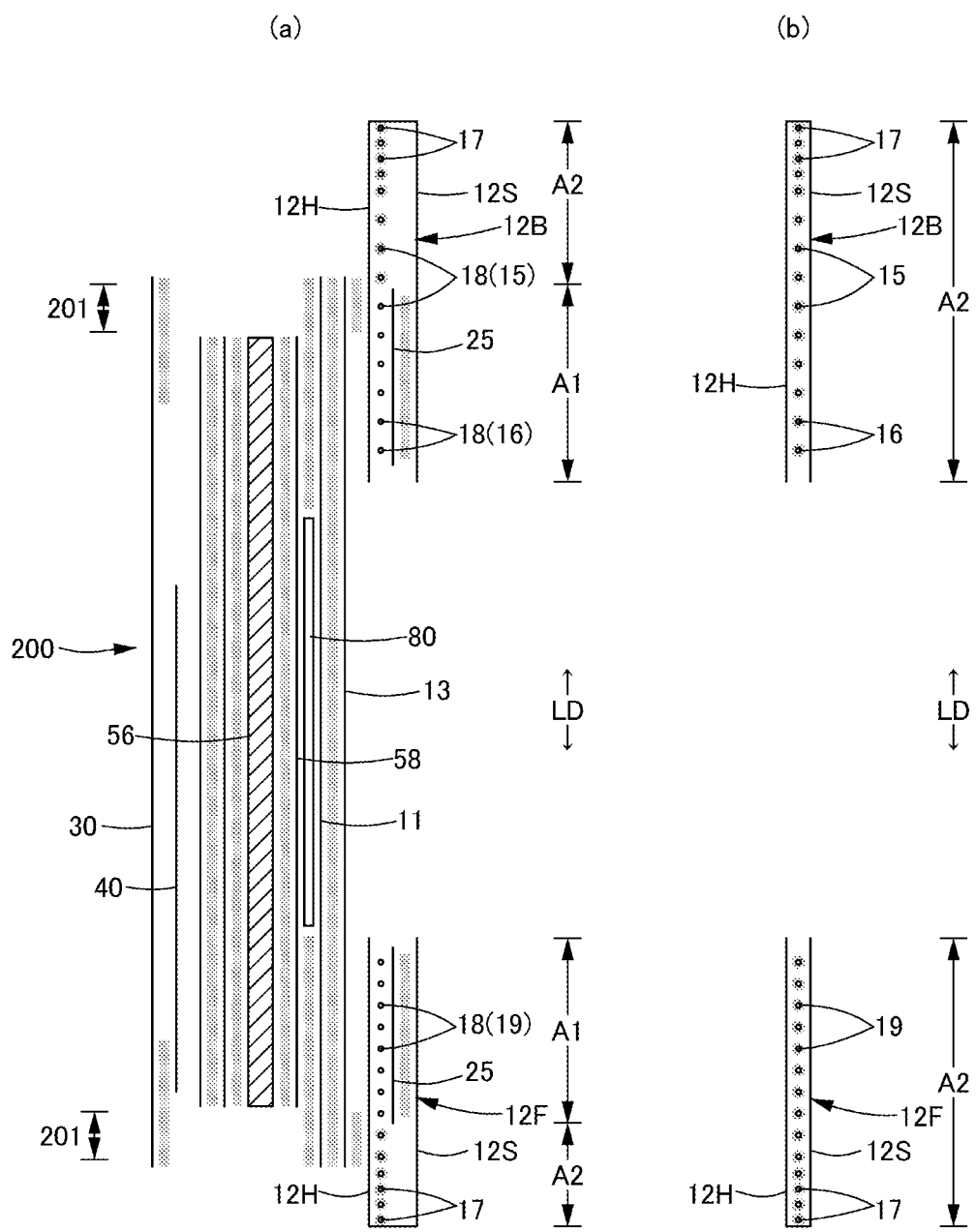
FIG. 10(a) is a cross-sectional view taken along line 4-4 in FIG. 9.
FIG. 10(b) is a cross-sectional view taken along line 5-5 in FIG. 9.

As illustrated in FIGS. 9 and 10, one preferred embodiment is that at least either of the front side outer member 12F and the back side outer member 12B is joined to the inner member 200 at regions overlapping with both the end portions in the width direction of the inner member 200, and is not joined or is intermittently and peelably joined to the inner member 200 at a part on a crotch side or a whole part in the front-back direction LD of a region between the regions overlapping with the both end portions in the width direction of the inner member 200. In this case, a gap between the inner member 200 and at least one of the front side outer member 12F and the back side outer member 12B communicates with the crotch side to improve air permeability. In addition, since the cover nonwoven fabric 13 (perforated nonwoven fabric) hidden by at least one of the front side outer member 12F and the back side outer member 12B can be directly seen by pulling up this part, the high visual effect of the holes 14 can be obtained.

Explanation of Terms Used Herein

The following terms in the specification have the following meanings unless otherwise specified in the specification.

"Front-back (longitudinal) direction" means a direction connecting the ventral side (front side) and the dorsal side (back side). "Width direction" means a direction orthogonal to the front-back direction (right-left direction).

"Front surface side" means a side closer to the skin of a wearer wearing an underpants-type disposable diaper, and "back surface side" means a side far from the skin of a wearer wearing an underpants-type disposable diaper.

"Front surface" means a surface of a member closer to the skin of a wearer wearing an underpants-type disposable diaper, and "back surface" means a surface far from the skin of a wearer wearing an underpants-type disposable diaper.

"Total luminous transmittance" means a value measured according to JIS-K 7105 for total luminous transmittance.

"Area rate" means a rate of a target portion to a unit area and is expressed as a percentage obtained by dividing a total area of target portions (for example, the holes) in a target region (for example, a cover nonwoven fabric) by an area of the target region. In a mode in which a large number of the target portions are provided at intervals, it is desirable to set the size of the target region such that ten or more target portions are included therein and obtain the area rate. For example, the area rate of the holes can be measured by the following procedure, for example, using the trade name VHX-1000 manufactured by KEYENCE CORPORATION under a measurement condition of magnification of ×20.

(1) Set a lens with a magnification of ×20 and adjust a focus. Adjust the position of a nonwoven fabric such that 4 holes×6 holes come in sight.

(2) Specify the brightness of "hole" and measure the area of the hole.

(3) Click extraction color of [Area Measurements] in [Measurement/Comment]. Click "hole".

(4) Click [Block Measurement], check [Displaying the measurement result window] and save the measurement result as CSV data.

"Stretch rate" means the value relative to the natural length (100%).

"Gel strength" is measured as follows: A super absorbent polymer of 1.0 g is added to artificial urine of 49.0 g (mixture of urea: 2 wt %, sodium chloride: 0.8 wt %, calcium chloride dihydrate: 0.03 wt %, magnesium sulfate heptahydrate: 0.08 wt %, and ion exchanged water: 97.09 wt %) and the mixture is stirred with a stirrer. After leaving generated gel for three hours in a thermo hygrostat bath at 40° C.×60% RH, the gel is cooled to room temperature, and the gel strength of the gel is measured with Curdmeter (MAX ME-500, manufactured by I. Techno Engineering Co., Ltd).

"Basis weight" is measured as follows. After the sample or test piece is preliminarily dried, it is allowed to stand in a test chamber or equipment under the normal conditions (the test location is at a temperature of 20±5° C. and with a relative humidity of 65% or less) until the constant mass. The preliminary drying is to make the sample or test piece be constant mass in an environment not exceeding a temperature of 50° C. and a relative humidity of 10 to 25%. For fibers with an official moisture regain of 0.0%, preliminary drying may not be performed. A sample of dimensions of 200 mm×250 mm (±2 mm) is cut using a cutting template (200 mm×250 mm, ±2 mm) from the test piece in the constant mass. The basis weight is set by weighing the sample, multiplying by 20, and calculating the weight per one square meter.

"Thickness" is automatically measured under the conditions of a load of 10 gf/cm$^2$ and a pressing area of 2 cm$^2$ using an automatic thickness measuring device (KES-G5 handy compression measurement program).

"Water absorption capacity" is measured according to JIS K7223-1996 "Testing method for water absorption capacity of super absorbent polymers".

"Water absorption rate" is the "time that elapses before the end point" when JIS K7224-1996 "Testing method for water absorption rate of super absorbent polymers" has been carried out using 2 g of superabsorbent polymers and 50 g of physiological saline solution.

"Spread state" means a flatly spread state without contraction or slack.

The dimension of each part means the dimension in the spread state, not the natural length state, unless otherwise stated.

When environmental conditions in tests and measurements are not described, the tests and measurements shall be carried out in a test room or apparatus under normal conditions (the test location is at a temperature of 20±5° C. and with a relative humidity of 65% or less).

INDUSTRIAL APPLICABILITY

The present invention is applicable to an underpants-type disposable diaper.

REFERENCE SIGNS LIST 11 liquid impervious sheet
12A side seal portion
12B back side outer member
12F front side outer member
12H inner sheet layer
12S outer sheet layer
13 cover nonwoven fabric
14 hole
18 idle elastic member
200 inner member
201 inner and outer joined portion
25 outer decorative sheet
27, 28 decorative printing
27 outer decorative printing
28 inner decorative printing
29 registration mark
30 top sheet
40 intermediate sheet
50 absorbent element
56 absorber
58 wrapping sheet
60 side gather
62 gather nonwoven fabric
80 indicator
A1 non-stretchable region
A2 stretchable region
C gluteal cover portion
L intermediate region
LD front-back direction
LO leg opening
T lower torso region
U under-waist portion
W waist portion
WD width direction
WO waist opening

The invention claimed is:

1. An underpants-type disposable diaper, in which a front side outer member disposed in a front body and a back side outer member disposed in a back body are separately provided, the front side outer member and the back side outer member are spaced apart in the front-back direction at the middle in the front-back direction,
    an inner member having a liquid pervious top sheet, a liquid impervious sheet, and an absorber interposed therebetween extends in the front-back direction from the front side outer member to the back side outer member, the inner member is joined to each of the front side outer member and the back side outer member,
    a cover nonwoven fabric covering a back surface of the inner member is provided from between the front side outer member and the inner member to between the back side outer member and the inner member,
    both sides of the front side outer member and both sides of the back side outer member are joined to each other, a waist opening and a pair of right and left leg openings are included, and
    elastic members are incorporated in the front side outer member and the back side outer member,
    wherein the cover nonwoven fabric is provided with a plurality of holes penetrating a front surface and a back surface of the cover nonwoven fabric from between the front side outer member and the inner member to between the back side outer member and the inner member at intervals,
    wherein the front side outer member and the back side outer member have, at least at portions overlapping with the cover nonwoven fabric and not having any elastic member, a total luminous transmittance of 50% or more,
    wherein the underpants-type disposable diaper comprises side gathers extending from both sides of the inner member so as to be in contact with the legs of a wearer and each of the side gathers having a base end on a side portion on a back surface side of the liquid impervious sheet in the inner member, and a gather nonwoven fabric forming an outer surface at least from the base end to a tip end,
    wherein the cover nonwoven fabric extends at least from between a base portion of one of the side gathers and the liquid impervious sheet to between a base portion of the other side gather and the liquid impervious sheet, and
    wherein the gather nonwoven fabric has a total luminous transmittance of 60 to 90%.

2. The underpants-type disposable diaper according to claim 1, comprising inner decorative printing, which is visible on outer surfaces of the front side outer member and the back side outer member, on the liquid impervious sheet at least in a region thereof, which overlaps the front side outer member and the back side outer member,
    wherein the inner decorative printing overlaps with the holes at least in a part of the cover nonwoven fabric.

3. The underpants-type disposable diaper according to claim 2, wherein at least either of the front side outer member and the back side outer member is joined to the inner member, at regions overlapping with both end portions in the width direction of the inner member, and is not joined or is intermittently and peelably joined to the inner member, at a part on a crotch side or a whole part in the front-back direction of a region between the regions overlapping with the both end portions in the width direction of the inner member.

4. The underpants-type disposable diaper according to claim 2, wherein at least either of a region where the front side outer member and the cover nonwoven fabric overlap with each other and a region where the back side outer member and the cover nonwoven fabric overlap with each other includes, on an outer side of the cover nonwoven fabric, a portion provided with an outer decorative sheet having outer decorative printing and a portion not having the outer decorative sheet.

5. The underpants-type disposable diaper according to claim 4, wherein the inner decorative printing is a continuous decorative printing comprising a plurality of elements regularly repeating in the front-back direction and the width direction, and the outer decorative printing is an intermittent decorative printing arranged only in one or both of front and back sides of a product.

6. The underpants-type disposable diaper according to claim 5, wherein at least either of the front side outer member and the back side outer member is joined to the inner member, at regions overlapping with both end portions in the width direction of the inner member, and is not joined or is intermittently and peelably joined to the inner member, at a part on a crotch side or a whole part in the front-back direction of a region between the regions overlapping with the both end portions in the width direction of the inner member.

7. The underpants-type disposable diaper according to claim 4, wherein at least either of the front side outer member and the back side outer member is joined to the inner member, at regions overlapping with both end portions in the width direction of the inner member, and is not joined or is intermittently and peelably joined to the inner member, at a part on a crotch side or a whole part in the front-back direction of a region between the regions overlapping with the both end portions in the width direction of the inner member.

8. The underpants-type disposable diaper according to claim 1, wherein at least either of the front side outer member and the back side outermember is joined to the inner member, at regions overlapping with both end portions in the width direction of the inner member, and is not joined or is intermittently and peelably joined to the inner member, at a part on a crotch side or a whole part in the front-back direction of a region between the regions overlapping with the both end portions in the width direction of the inner member.

* * * * *